(12) United States Patent
deLong et al.

(10) Patent No.: US 9,180,080 B2
(45) Date of Patent: Nov. 10, 2015

(54) CHIRAL COMPOUNDS, COMPOSITIONS, PRODUCTS AND METHODS EMPLOYING SAME

(71) Applicant: Merz North America, Inc., Greensboro, NC (US)

(72) Inventors: Mitchell A. deLong, Chapel Hill, NC (US); Kalla Lynn Kvalnes, Cambridge, MD (US); Raymond Boissy, Cincinnati, OH (US)

(73) Assignee: MERZ NORTH AMERICA, INC., Greensboro, NC (US)

( * ) Notice: Subject to any disclaimer, the term of this patent is extended or adjusted under 35 U.S.C. 154(b) by 0 days.

(21) Appl. No.: 13/734,678

(22) Filed: Jan. 4, 2013

(65) Prior Publication Data

US 2013/0224136 A1 Aug. 29, 2013

Related U.S. Application Data

(60) Provisional application No. 61/583,246, filed on Jan. 5, 2012.

(51) Int. Cl.
| | |
|---|---|
| A61K 8/60 | (2006.01) |
| C07D 311/94 | (2006.01) |
| A61K 8/49 | (2006.01) |
| C07D 493/04 | (2006.01) |
| A61Q 19/02 | (2006.01) |
| C07D 313/04 | (2006.01) |
| C07D 215/227 | (2006.01) |
| C07D 335/02 | (2006.01) |
| C07D 333/32 | (2006.01) |
| C07D 333/64 | (2006.01) |
| C07H 15/203 | (2006.01) |
| C07D 313/18 | (2006.01) |
| C07D 309/10 | (2006.01) |
| C07D 309/12 | (2006.01) |
| C07D 311/02 | (2006.01) |
| C07D 215/22 | (2006.01) |
| C07D 319/12 | (2006.01) |
| C07D 333/48 | (2006.01) |
| C07D 307/20 | (2006.01) |
| A61K 8/33 | (2006.01) |

(52) U.S. Cl.
CPC . *A61K 8/602* (2013.01); *A61K 8/33* (2013.01); *A61K 8/498* (2013.01); *A61K 8/4926* (2013.01); *A61K 8/4973* (2013.01); *A61K 8/4986* (2013.01); *A61Q 19/02* (2013.01); *C07D 215/22* (2013.01); *C07D 215/227* (2013.01); *C07D 307/20* (2013.01); *C07D 309/10* (2013.01); *C07D 309/12* (2013.01); *C07D 311/02* (2013.01); *C07D 311/94* (2013.01); *C07D 313/04* (2013.01); *C07D 313/18* (2013.01); *C07D 319/12* (2013.01); *C07D 333/32* (2013.01); *C07D 333/48* (2013.01); *C07D 333/64* (2013.01); *C07D 335/02* (2013.01); *C07D 493/04* (2013.01); *C07H 15/203* (2013.01)

(58) Field of Classification Search
USPC .......................................................... 549/416
See application file for complete search history.

(56) References Cited

U.S. PATENT DOCUMENTS

| | | | |
|---|---|---|---|
| 5,585,525 | A | 12/1996 | Carter et al. |
| 5,811,593 | A | 9/1998 | Carter et al. |
| 5,932,196 | A | 8/1999 | Motley et al. |
| 6,068,834 | A | 5/2000 | Kvalnes et al. |
| 6,139,854 | A | 10/2000 | Kawato |
| 6,258,344 | B1 | 7/2001 | Venkateswaran |
| 6,294,186 | B1 | 9/2001 | Beerse et al. |
| 6,497,860 | B1 | 12/2002 | Kawato et al. |
| 6,537,527 | B1 | 3/2003 | Kvalnes et al. |
| 2007/0207116 | A1 | 9/2007 | Brown |
| 2009/0216002 | A1 | 8/2009 | Kleinebekel et al. |
| 2010/0303747 | A1 | 12/2010 | Hattendorf et al. |
| 2013/0224137 | A1 | 8/2013 | Kvalnes et al. |

OTHER PUBLICATIONS

Boissy et al. "DeoxyArbutin: a novel reversible tyrosinase inhibitor with effective in vivo skin lightening potency" Exp. Dermatol. 2005, 14(8), 601-608.
Chawla et al. "DeoxyArbutin and its Derivatives Inhibit Tyrosinase Activity and Melanin Synthesis Without Inducing Reactive Oxygen Species or Apoptosis" J. Drugs Dermatol. 2012, 11(10), pp. e28-34.
Chawla et al. "Mechanism of tyrosinase inhibition by deoxyArbutin and its second-generation derivatives" Br. J. Dermatol. 2008, 159(6), 1267-1274.
Hamed et al. "Comparative efficacy and safety of deoxyarbutin, a new tyrosinase-inhibiting agent" J. Cosmet. Sci. 2006, 57(4), 291-308.

(Continued)

*Primary Examiner* — Kristin Vajda

(74) *Attorney, Agent, or Firm* — Choate, Hall & Stewart LLP; Charles E. Lyon; Kevin M. Henry

(57) ABSTRACT

Compounds that function, alone or in combination, as inhibitors of pigmentation for the improvement of mammalian skin are described herein. Specifically, the compounds of the present disclosure, namely chiral, non-racemic compounds, function as pigment formation inhibitors thereof to beautify skin and discourage the production of melanins. One or more products, consumer and otherwise, comprising the chiral, non-racemic compounds are disclosed herein. Methods of employing both the compounds of the present disclosure and the products incorporating the present compounds are also disclosed herein.

23 Claims, 7 Drawing Sheets

(56) References Cited

OTHER PUBLICATIONS

Hamed et al. "Effect of Deoxyarbutin on Melanogenesis: In Vivo Comparision with other Melanogenesis Inhibitor" J. Cosmet. Sci. 2004, 55(1), 118-119.

Hu et al. "Effects of hydroquinone and its glucoside derivatives on melanogenesis and antioxidation: Biosafety as skin whitening agents" J. Dermatol. Sci. 2009, 55(3), 179-184.

Lin et al. "Study on the Stability of DeoxyArbutin in an Anhydrous Emulsion System" Int. J. Mol. Sci. 2011, 12(9) 5946-5954.

Yang et al. "Determination of the Thermodegradation of deoxyArbutin in Aqueous Solution by High Performance Liquid Chromatography" Int. J. Mol. Sci. 2010, 11(10), 3977-3987.

PCT/US2013/20356 International Search Report and Written Opinion dated Apr. 26, 2013 (16 pages).

No Author Listed, Aquaplant, Dissolved Oxygen, 2 pages http://aquaplant.tamu.edu/faq/dissolved-oxygen/ (2014).

CHIRAL COMPOUNDS, COMPOSITIONS, PRODUCTS AND METHODS EMPLOYING SAME

CROSS-REFERENCE TO RELATED APPLICATION

This application claims priority to U.S. Provisional Patent Application No. 61/583,246, filed on Jan. 5, 2012, the entire contents of which are hereby incorporated by reference.

FIELD OF THE DISCLOSURE

The present disclosure relates to compounds that function, alone or in combination, as pigmentation inhibitors for mammalian, and particularly human, skin. Specifically, the compounds of the present disclosure, namely single-enantiomer or largely single-enantiomer forms of hitherto racemic hydroxybenzene compounds, are useful for reducing pigmentation and otherwise beautifying the skin. The present disclosure further relates to one or more products, consumer and otherwise, comprising the compounds disclosed herein. The present disclosure encompasses pharmaceutical and cosmetic methods of employing both the compounds of the present disclosure and products incorporating the present compounds.

INTRODUCTION

Humans continue to demonstrate an obsession with appearance, particularly of the face, but increasingly of the skin and body in general. Indeed, many believe that appearance is intrinsically linked to self-esteem, the selection of a significant other, professional advancement and overall societal acceptance. Consequently, the demand for appearance-enhancing alternatives continues to increase, as evidenced by the advent of many new products and services, each of which purports to achieve a desired appearance-enhancing result. Nevertheless, the majority of products and services that have been developed to address this growing need are designed to conceal rather than improve the appearance of skin. Conventional solutions to this dilemma have generally sought to disguise skin imperfections with, for example, opaque products that cover the skin and mask its visual appearance.

Despite providing a partial solution to the dilemma of appearance, conventional skin enhancing products have yet to significantly address the escalation of physical ailments associated with a given skin condition. As skin imperfections become more prevalent in humans, particularly those experiencing advanced aging, so too does the onset of physical ailments and disease. Thus, researchers have increasingly engaged in more sophisticated attempts to develop compositions that actually improve, rather than simply conceal, skin imperfections. Such compositions not only serve to enhance the visual appearance of skin, but further address the incidence of true skin disorders, including but not limited to conditions such as melasma, chloasma, pigmented spots, lentigo senilis, freckles, café au lait spots, liver spots, pigmented keratosis, ephelides, post-inflammatory or post surgical hyperpigmentation, periorbital darkening, mottling, and solar lentigens. Disorders characterized by areas of too little pigmentation include but are not limited to, vitiligo, piebaldism, leukoderma, and nevus depigmentosis.

Notwithstanding previous efforts, little progress has been made in this realm of skin care. This minimal advancement is primarily due to a lack of understanding of the processes that influence the appearance and maintenance of human skin. Indeed, researchers have generally relied upon the haphazard discovery of purported skin-enhancing alternatives, rather than the manipulation of underlying theories and synergies, to thwart the pigmentation disorders of mammalian skin. Attempts to improve the condition of mammalian skin have failed to address the specific and diversified needs of consumers. Consequently, consumers have continued to rely upon the use and development of appearance-concealing alternatives.

SUMMARY

Thus, in one aspect, compounds for beautifying and improving the condition of mammalian skin are disclosed. Said compounds function, alone and in combination, as pigmentation inhibitors of mammalian skin. In application, chiral, non-racemic compounds of the present disclosure function to beautify mammalian skin. Specifically, the compounds disclosed herein are adapted to inhibit skin pigmentation and discourage melanin formation upon application to mammalian skin.

In another aspect, combinations of the present compounds may be employed to beautify and improve the condition of mammalian skin. Indeed, it has been surprisingly discovered that certain deoxyArbutin analog compounds, which individually demonstrate skin-enhancing activity in vitro and in vivo, may convey synergistic benefits upon employment in combination.

In another aspect, products incorporating the compounds of the present disclosure are disclosed. Such products may take an assortment of shapes and forms depending on the precise application for which deployment of the product is desired and the needs and/or abilities of the formulator. The products of the present disclosure may be effective in beautifying and improving mammalian skin, e.g., by discouraging the formation of melanin therein. The products may be adapted to convey actual skin care benefits to the substrates to which they are applied, rather than simply conceal skin imperfections like conventional skin care products.

In another aspect, methods of using the compounds and products of the present disclosure are disclosed. The methods may be adapted to provide enhanced or permanent beautification benefits to mammalian, and particularly human, skin.

In some embodiments, other active and/or adjunct ingredients are added, such as for a sunscreen or a sunblock formulation, so that the topical formulae has the further advantage of preventing further sun damage and/or solar stimulation of pigmentation. Preferred formulae of these types have an SPF value of 15 or higher.

Suitable parenterally administered formulations include sterile aqueous solutions, dispersions, and sterile powders. The carrier employed can be a solvent or a dispersing medium. Additionally, additives that enhance the stability, sterility, and isotonicity of the compositions, including antimicrobial preservatives, antioxidants, chelating agents and buffers may be added.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference. Further, while particular embodiments of the subject disclosure have been described, it would be obvious to those skilled in the art that various changes and modifications to the compositions disclosed herein can be made without departing from the spirit and scope of the disclosure.

DETAILED DESCRIPTION

Figure 1:
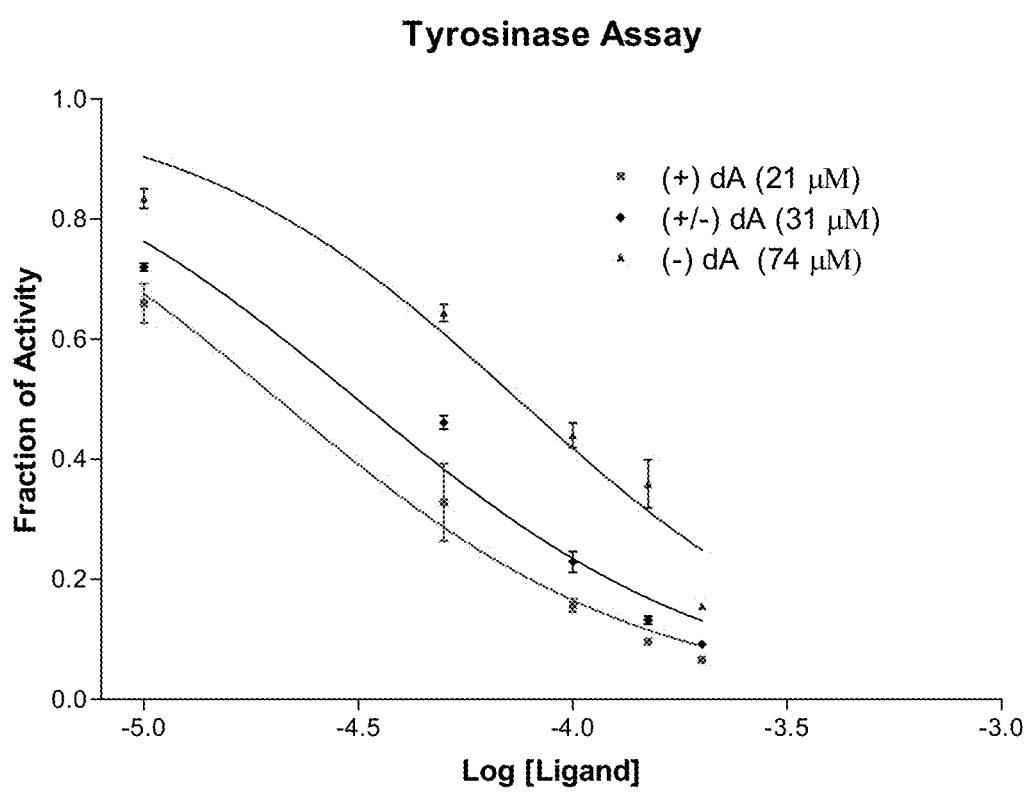
FIG. 1 is a graph illustrating the combined employment of two different pigmentation analogs in vitro.

A thorough understanding of the theories underlying the pigmentation of mammalian, and particularly human, skin has led to the surprising identification of compounds that can improve mammalian skin conditions. In particular, it has been surprisingly discovered that a class of compounds can be improved by separating the hitherto inseparable optical forms to enhance the condition of mammalian skin—namely, deoxyArbutin compounds. Indeed, the compounds of the present disclosure function, alone and in combination, as pigmentation inhibitors that improve mammalian skin. The compounds of the present disclosure are adapted to encourage mammalian skin lightening. Further, it has been surprisingly discovered that notable synergy is achieved via the combined employment of two or more analogs from the same or different groups.

The present disclosure addresses problems associated with the employment of conventional skin care compositions and/or products. It has been surprisingly discovered that the employment of specific compounds, both individually and in combination, serve to enhance and beautify mammalian, and particularly human, skin. Indeed, the compounds of the present disclosure constitute an actual and viable advancement in the realm of skin care, particularly as traditional skin care compositions have sought to simply conceal, rather than improve the condition of mammalian skin. Specifically, it has been surprisingly discovered that the compounds of the present disclosure serve to convey numerous beautification benefits to human skin while discouraging the onset of skin disease and minimizing irritation. Irritation, when observed, is found in both chiral forms, while the efficacy is found predominantly in a single form.

DEFINITIONS AND USAGE OF TERMS

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

A "deoxyArbutin compound" refers to a compound that contains a mixed-ketal group, in which one oxygen atom of the mixed ketal group is substituted with a parahydroxyphenyl group (substituted or unsubstituted) and the other oxygen is substituted with a carbon ring or chain (e.g., a substituted or unsubstituted alkyl, heteroalkyl, alkenyl, alkynyl, aryl or heteroaryl group). As those skilled in the art will appreciate, a mixed-ketal group refers to a moiety in which a central carbon atom is attached via single bonds to two oxygen atoms. In a deoxyArbutin compound, the center carbon must have at least one of its two remaining valences substituted by a carbon ring or chain (e.g., a substituted or unsubstituted alkyl, heteroalkyl, alkenyl, alkynyl, aryl or heteroaryl group). Exemplary deoxyArbutin compounds include compounds of formulae (I), (Ia) and (Ib) described herein. The term "deoxyArbutin" when used alone specifically refers to the compound 4-(tetrahydro-2H-pyran-2-yloxy)phenol. The terms "deoxyArbutin" and "deoxyArbutin compound" include deoxyArbutin and deoxyArbutin compounds in all isomeric forms (e.g., enantiomeric and diastereomeric forms) and mixtures thereof. For example, deoxyArbutin refers to (R)-4-(tetrahydro-2H-pyran-2-yloxy)phenol, (S)-4-(tetrahydro-2H-pyran-2-yloxy)phenol, and mixtures thereof in any ratios.

"Chiral, non-racemic" is intended to encompass compounds that contain at least one chiral center, and do not have equal amounts of both enantiomers. It is contemplated explicitly herein, that the percent enantiomeric excess (% ee) of the more potent and more useful chiral form, will be from about 0.01% ee to about 100% ee. "Chiral, non-racemic" is intended to encompass compounds of the (+) as well as (−) optical activity, as each has utility independently, as well as in all admixtures as described above.

"Beautification" is intended to encompass at least one of the reduction of imperfections in mammalian skin (e.g., pigmentation), and an increase in the overall appearance of youthfulness.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. Substituents may also be themselves substituted. When substituted, the substituent group may be (but is not limited to) $C_1$-$C_4$ alkyl, aryl, amino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. Substituents may also be themselves substituted. When substituted, the substituent group may be, e.g., alkyl, halogen or alkoxy. Substituents may also be themselves substituted. Substituents be placed on the alkene itself and also on the adjacent member atoms or the alkynyl moiety "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. When substituted, the substituent group may be, e.g., alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the group —C(O)R wherein R is alkyl; alkenyl; alkyl alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl "Amino" refers to the group —NR'R' wherein each R' is, independently, hydrogen, alkyl, aryl, heteroaryl, $C_1$-$C_4$ alkyl aryl or $C_1$-$C_4$ alkyl heteroaryl. The two R' groups may themselves be linked to form a ring.

"Aryl" refers to an aromatic carbocyclic group. "Aryl" may be exemplified by phenyl. The aryl group may be substituted or unsubstituted. Substituents may also be themselves substituted. When substituted, the substituent group is may be, e.g., heteroaryl, acyl, carboxyl, carbonylamino, nitro, amino, cyano, halogen, or hydroxyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

"Carboxyl" refers to the group —C(=O)O—$C_1$-$C_4$ alkyl.

"Carbonylamino" refers to the group —C(O)NR'R' wherein each R' is, independently, hydrogen, alkyl, aryl, cycloalkyl; heterocycloalkyl; heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" refers to a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, such as 4 to 7 carbon atoms or 5 to 6 carbon atoms in the ring. Bicyclic carbocyclic groups contain 8 to 12 carbon atoms, such as 9 to 10 carbon atoms in the ring. Carbocyclic groups may be substituted or unsubstituted. Substituents may also be themselves substituted. Carbocyclic groups include but are not limited to cyclopropyl, cyclobutyl, cyclopentyl, cyclohexyl, cyclohexenyl, and cycloheptyl. Suitable carbocyclic groups include cyclopropyl and cyclobutyl. Carbocyclic groups are not aromatic.

"Halogen" refers to fluoro, chloro, bromo or iodo moieties. Suitably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. When substituted, the substituents may themselves be substituted. Substituents include but are not limited to aryl; $C_1$-$C_4$ alkylaryl; amino; halogen, hydroxy, cyano, nitro; carboxyl; carbonylamino or $C_1$-$C_4$ alkyl. Suitable heteroaromatic groups include tetrazoyl, triazolyl; thienyl, thiazolyl, purinyl, pyrimidyl, pyridyl, furanyl, benzothiofuranyl, thienyl, furanyl, tetrazoyl, triazolyl and pyridyl.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

"Heteroalkyl" refers to an alkyl group in which at least one carbon atom is replaced with a heteroatom. An exemplary heteroalkyl group is a methoxymethyl group.

"Heteroatom" refers to an atom other than carbon in the ring of a heterocyclic group or a heteroaromatic group or the chain of a heteroalkyl group. Suitably, heteroatoms are selected from the group consisting of nitrogen, sulfur, and oxygen atoms. Groups containing more than one heteroatom may contain the same or different heteroatoms.

"Heterocarbocyclic group" or "heterocycloalkyl" or "heterocyclic" means a monovalent saturated or partially unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, suitably 4 to 7 carbon atoms or 5 to 6 carbon atoms in the ring. Bicyclic heterocarbocyclic groups contain 8 to 12 carbon atoms, e.g., 9 to 10 carbon atoms in the ring. Heterocarbocyclic groups may be substituted or unsubstituted. Substituents may also be themselves substituted. Exemplary heterocarbocyclic groups include epoxy, tetrahydrofuranyl, azacyclopentyl, azacyclohexyl, piperidyl, homopiperidyl, piperidyl, and homopiperidyl. A suitable heterocarbocyclic group is piperidyl.

"Hydroxy" or "hydroxyl" refers to —OH. Alcohols contain hydroxy groups. Hydroxy groups may be free or protected.

"Linker" means a linear chain of n member atoms where n is an integer of from 1 to 4.

"Member atom" means a carbon, nitrogen, oxygen or sulfur atom. Member atoms may be substituted up to their normal valence. If substitution is not specified the substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Sulfonyl" refers to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl or $C_1$-$C_4$ alkyl heteroaryl.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$;

—(CH$_2$)$_{0-4}$S(O)$_2$OR$^\circ$; —(CH$_2$)$_{0-4}$OS(O)$_2$R$^\circ$; —S(O)$_2$NR$^\circ{}_2$; —(CH$_2$)$_{0-4}$S(O)R$^\circ$; —N(R$^\circ$)S(O)$_2$NR$^\circ{}_2$; —N(R$^\circ$)S(O)$_2$R$^\circ$; —N(OR$^\circ$)R$^\circ$; —C(NH)NR$^\circ{}_2$; —P(O)$_2$R$^\circ$; —P(O)R$^\circ{}_2$; —OP(O)R$^\circ{}_2$; —OP(O)(OR$^\circ$)$_2$; SiR$^\circ{}_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

"Pharmaceutically or cosmetically acceptable carrier" means a carrier that is useful for the preparation of a pharmaceutical composition that is at least one of: generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal, intramuscular, sublingual, nasal and oral administration. "Pharmaceutically or cosmetically acceptable carrier" also includes agents for preparation of aqueous dispersions and sterile powders for injection or dispersions.

"Excipient" includes physiologically compatible additives useful in preparation of a pharmaceutical composition. Examples of pharmaceutically or cosmetically acceptable carriers and excipients can for example be found in Remington Pharmaceutical Science, 16th Ed.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\text{alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

"Therapeutically effective amount" as used herein refers to a dosage of the compounds or compositions effective for influencing, reducing or inhibiting the activity of or preventing activation melanocytes. This term as used herein may also refer to an amount effective at bringing about a desired in vivo effect in an animal (e.g., a human), such as reduction in overall pigmentation, or a local reduction in pigmentation.

"Administering" refers to administration of the compounds as needed to achieve the desired effect.

The term "disease or condition associated with melanin formation" is used to mean a disease or condition treatable, in whole or in part, by inhibition of pigment formation.

The term "controlling the disease or condition" is used to mean changing the activity of one or more enzymes to affect the disease or condition.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended. With respect to amounts of components, all percentages are by weight, unless explicitly indicated otherwise.

Compounds

Compounds that may beautify and improve the appearance and condition of mammalian skin are disclosed. Indeed, the disclosed compounds of the present may alter, in vitro as well as in vivo, the amount of pigment produced by the skin and thus, convey numerous beautification benefits to human skin while discouraging the onset of skin disorders. Without wishing to be bound by theory, it is believed that the ability of the present compounds to discourage skin pigmentation is due, at least in part, to the compounds' ability to inhibit the enzymes known as tyrosinase/dopa oxidase, as well as their ability to resist oxidation by those same enzymes. The ability of the present compounds to inhibit melanin formation at the very beginning of the process helps to ensure that they may safely be administered to subjects. Whether employed individually or in combination, the compounds of the present disclosure may exhibit heightened performance and synergy in the beautification of mammalian skin.

Chiral, Non-Racemic Compounds

Certain chiral, non-racemic compounds have been identified and deployed, and may be adapted to convey material beautification and improvement benefits to the mammalian skin onto which they are applied. The compounds disclosed herein are adapted to actually improve mammalian skin, rather than simply conceal skin imperfections. Previously, researchers have generally sought to mask, rather than improve, the condition of mammalian skin via, for example, the use of opaque chemicals. The present compounds, and the synergy achieved via their practice, further serve the fundamental goal of preventing the onset of physical ailments and irritation of the mammalian skin to which they are applied.

In some embodiments, the present invention provides a compound of formula I or formula II, as described in detail below and herein, that is enantiomerically enriched. As used herein, the term "enantiomerically enriched", as used herein signifies that one enantiomer makes up at least 80% or 85% of the preparation. In certain embodiments, the term enantiomerically enriched signifies that at least 90% of the preparation is one of the enantiomers. In other embodiments, the term signifies that at least 95% of the preparation is one of the enantiomers.

In certain embodiments, the present invention provides a compound of formula I having a % enantiomeric excess (% ee) of at least 50%. In certain embodiments, the present invention provides a compound of formula I having a % enantiomeric excess (% ee) of at least 60%. In certain embodiments, the present invention provides a compound of formula I having a % enantiomeric excess (% ee) of at least 70%. In certain embodiments, the present invention provides a compound of formula I having a % enantiomeric excess (% ee) of at least 80%. In certain embodiments, the present invention provides a compound of formula I having a % enantiomeric excess (% ee) of at least 90%. In some embodiments, the present invention provides a compound of formula I having a % ee of at least 95%. In some embodiments, the present invention provides a compound of formula I having a % ee of at least 98%. In some embodiments, the present invention provides a compound of formula I having a % ee of at least 99%.

In certain embodiments, the present invention provides a compound of formula II having a % enantiomeric excess (% ee) of at least 50%. In certain embodiments, the present invention provides a compound of formula II having a % enantiomeric excess (% ee) of at least 60%. In certain embodiments, the present invention provides a compound of formula II having a % enantiomeric excess (% ee) of at least 70%. In certain embodiments, the present invention provides a compound of formula II having a % enantiomeric excess (% ee) of at least 80%. In certain embodiments, the present invention provides a compound of formula II having a % enantiomeric excess (% ee) of at least 90%. In some embodiments, the present invention provides a compound of formula II having a % ee of at least 95%. In some embodiments, the present invention provides a compound of formula II having a % ee of at least 98%. In some embodiments, the present invention provides a compound of formula II having a % ee of at least 99%.

In certain embodiments, the present invention provides a compound of formula I, as defined and described herein, substantially free of a compound of formula II.

In certain embodiments, the present invention provides a compound of formula II, as defined and described herein, substantially free of a compound of formula I.

"Substantially free," as used herein, means that the compound is made up of a significantly greater proportion of one enantiomer. In other embodiments, at least about 95% by weight of a desired enantiomer is present. In still other embodiments of the invention, at least about 99% by weight of a desired enantiomer is present. Such enantiomers may be isolated from racemic mixtures by any method known to those skilled in the art, including high performance liquid chromatography (HPLC).

Accordingly, in one aspect, chiral, non-racemic compounds illustrated by the following general structures formula (I) and formula (II) are disclosed.

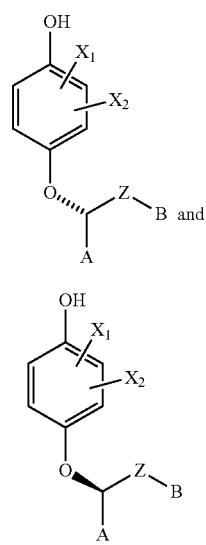

or a pharmaceutically acceptable salt thereof, wherein:
Z is selected from $NR_1$, S, O, SO and $SO_2$;
$R_1$ is selected from hydrogen and C1-6 aliphatic;
$X_1$ and $X_2$ are independently selected from hydrogen, halogen, cyano, nitro, optionally substituted C1-6 aliphatic, $—OR^2$, $—SR^2$, $—N(R^2)_2$, $—COOR^2$, and $—CON(R^2)_2$;
each $R^2$ is independently hydrogen or an optionally substituted C1-6 aliphatic; and
A and B are independently an optionally substituted group selected from C1-10 aliphatic, a 3-8 membered saturated or partially unsaturated carbocyclic ring, a 3-8 membered saturated or partially unsaturated heterocyclic ring having 1-2 heteroatoms independently selected from nitrogen, oxygen, and sulfur, phenyl, an 8-10 membered bicyclic aryl ring, a 5-6 membered heteroaryl ring having 1-4 heteroatoms independently selected from nitrogen, oxygen, and sulfur, or an 8-10 membered bicyclic heteroaryl ring having 1-4 heteroatoms independently selected from nitrogen, oxygen, or sulfur;
or A and B may be taken together with the atoms to which they are attached to form an optionally substituted saturated or partially unsaturated monocyclic or bicyclic ring having from 4-12 member atoms and 0-2 heteroatoms independently selected from nitrogen, oxygen, and sulfur.

Note that, other than in the chiral sense, both structures are identical, but they are drawn to specifically note the intention is to exemplify both enantiomers.

In another aspect, other optical isomers, diastereomers and enantiomers at chiral centers not explicitly depicted in the above formulae, as well as pharmaceutically-acceptable salts, biohydrolyzable amides, esters, and imides thereof are encompassed as suitable skin care agents herein. Said compounds also exhibit enhanced beautification and improvement benefits upon application to mammalian skin, while preventing the onset of physical ailments and irritation.

In some embodiments, the present invention provides a compound of formula I:

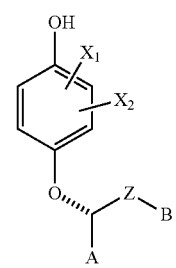

or a pharmaceutically acceptable salt thereof, wherein:
Z is selected from $NR_1$, S, O, SO and $SO_2$;
$R_1$ is selected from hydrogen and C1-6 aliphatic;
$X_1$ and $X_2$ are independently selected from hydrogen, halogen, cyano, nitro, optionally substituted C1-6 aliphatic, $—OR^2$, $—SR^2$, $—N(R^2)_2$, $—COOR^2$, and $—CON(R^2)_2$;
each $R^2$ is independently hydrogen or an optionally substituted C1-6 aliphatic; and
A and B are independently an optionally substituted group selected from C1-10 aliphatic, a 3-8 membered saturated or partially unsaturated carbocyclic ring, a 3-8 membered saturated or partially unsaturated heterocyclic ring having 1-2 heteroatoms independently selected from nitrogen, oxygen, and sulfur, phenyl, an 8-10 membered bicyclic aryl ring, a 5-6 membered heteroaryl ring having 1-4 heteroatoms independently selected from nitrogen, oxygen, and sulfur, or an 8-10 membered bicyclic heteroaryl ring having 1-4 heteroatoms independently selected from nitrogen, oxygen, or sulfur;
or A and B may be taken together with the atoms to which they are attached to form an optionally substituted saturated or partially unsaturated monocyclic or bicyclic ring having from 4-12 member atoms and 0-2 heteroatoms independently selected from nitrogen, oxygen, and sulfur.

In some embodiments, the present invention provides a compound of formula II:

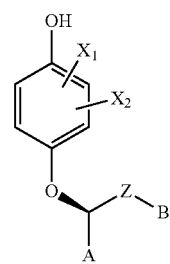

or a pharmaceutically acceptable salt thereof, wherein:
Z is selected from $NR_1$, S, O, SO and $SO_2$;
$R_1$ is selected from hydrogen and C1-6 aliphatic;
$X_1$ and $X_2$ are independently selected from hydrogen, halogen, cyano, nitro, optionally substituted C1-6 aliphatic, $—OR^2$, $—SR^2$, $—N(R^2)_2$, $—COOR^2$, and $—CON(R^2)_2$;

each $R^2$ is independently hydrogen or an optionally substituted C1-6 aliphatic; and A and B are independently an optionally substituted group selected from C1-10 aliphatic, a 3-8 membered saturated or partially unsaturated carbocyclic ring, a 3-8 membered saturated or partially unsaturated heterocyclic ring having 1-2 heteroatoms independently selected from nitrogen, oxygen, and sulfur, phenyl, an 8-10 membered bicyclic aryl ring, a 5-6 membered heteroaryl ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

or A and B may be taken together with the atoms to which they are attached to form an optionally substituted saturated or partially unsaturated monocyclic or bicyclic ring having from 4-12 member atoms and 0-2 heteroatoms independently selected from nitrogen, oxygen, and sulfur.

In certain embodiments, the Z group of formula I or II is O. In some embodiments, the Z group of formula I or II is $NR_1$. In some embodiments, the Z group of formula I or II is NH. In other embodiments, the Z group of formula I or II is SO. In some embodiments, the Z group of formula I or II is $SO_2$.

In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —$OR^2$, —$SR^2$, —$N(R^2)_2$, —$COOR^2$, and —$CON(R^2)_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In certain embodiments, the present invention provides a compound of either of formula I or II, wherein each of A and B is independently an optionally substituted group selected from C1-6 aliphatic, a 3-8 membered saturated or partially unsaturated carbocyclic ring, a 3-8 membered saturated or partially unsaturated heterocyclic ring having 1-2 heteroatoms independently selected from nitrogen, oxygen, or sulfur, phenyl, an 8-10 membered bicyclic aryl ring, a 5-6 membered heteroaryl ring having 1-4 heteroatoms independently selected from nitrogen, oxygen, and sulfur, or an 8-10 membered bicyclic heteroaryl ring having 1-4 heteroatoms independently selected from nitrogen, oxygen, or sulfur.

In some embodiments, the present invention provides a compound of either of formula I or II wherein A and B are taken together with the atoms to which they are attached to form an optionally substituted saturated or partially unsaturated ring having from 4-9 member atoms and 0-2 heteroatoms independently selected from nitrogen, oxygen, or sulfur.

In some embodiments, A and B of formula I or II are taken together to form a 5-8 member monocyclic ring having 0-2 heteroatoms independently selected from nitrogen, oxygen, and sulfur. In some embodiments, A and B of formula I or II are taken together to form a 5-6 member monocyclic ring having 0-1 heteroatoms independently selected from nitrogen, oxygen, and sulfur. In some embodiments, A and B of formula I or II are taken together to form a 5 member monocyclic ring. In some embodiments, A and B of formula I or II are taken together to form a 6 member monocyclic ring. Exemplary monocyclic rings formed by A and B are depicted in table of representative examples of chiral non-racemic compounds, below.

In certain embodiments, A and B of formula I or II are taken together to form an 8-12 member bicyclic ring having 0-2 heteroatoms independently selected from nitrogen, oxygen, and sulfur. In some embodiments, A and B of formula I or II are taken together to form 10 member bicyclic ring having 0-2 heteroatoms. Exemplary bicyclic rings formed by A and B are depicted in table of representative examples of chiral non-racemic compounds, below.

In some embodiments, the present invention provides a compound of formula I-a:

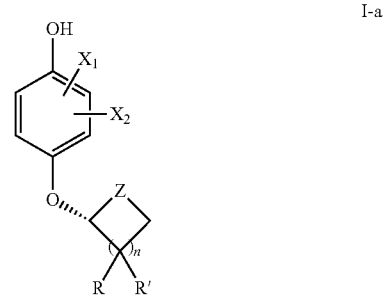

I-a or a pharmaceutically acceptable salt thereof, wherein Z, $X_1$ and $X_2$ are as defined and described above and herein, n is 1, 2, 3, 4 or 5, each R is independently selected from hydrogen and C1-6 aliphatic, and each R' is independently selected from hydrogen, C1-6 aliphatic and —$OR^a$, wherein each $R^a$ is independently selected from hydrogen and C1-6 aliphatic.

In some embodiments, n is 2, 3 or 4. In some embodiments, n is 2 or 3. In some embodiments, each occurrence of R and R' is hydrogen. In some embodiments, at least one occurrence of R' is —$OR^a$, wherein $R^a$ is hydrogen or C1-6 aliphatic (e.g., methyl). In some embodiments, In some embodiments, Z is O. In some embodiments, Z is S. In some embodiments, Z is SO. In some embodiments, Z is $SO_2$. In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —$OR^2$, —$SR^2$, —$N(R^2)_2$, —$COOR^2$, and —$CON(R^2)_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In some embodiments, the present invention provides a compound of formula I-a, substantially free of a compound of formula II-a.

In some embodiments, the present invention provides a compound of formula I-b:

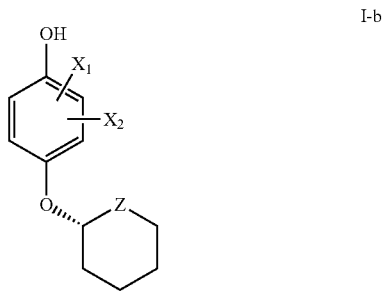

I-b or a pharmaceutically acceptable salt thereof, wherein Z, $X_1$ and $X_2$ are as defined and described above and herein.

In some embodiments, Z is O. In some embodiments, Z is S. In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —OR$^2$, —SR$^2$, —N(R$^2$)$_2$, —COOR$^2$, and —CON(R$^2$)$_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In some embodiments, the present invention provides a compound of formula I-b, substantially free of a compound of formula II-b.

In some embodiments, the present invention provides a compound of formula I-c:

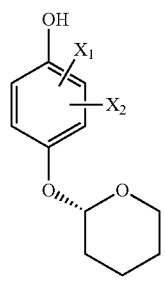

I-c or a pharmaceutically acceptable salt thereof, wherein $X_1$ and $X_2$ are as defined and described above and herein.

In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —OR$^2$, —SR$^2$, —N(R$^2$)$_2$, —COOR$^2$, and —CON(R$^2$)$_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In some embodiments, the present invention provides a compound of formula I-c, substantially free of a compound of formula II-c.

In some embodiments, the present invention provides a compound of formula I-d:

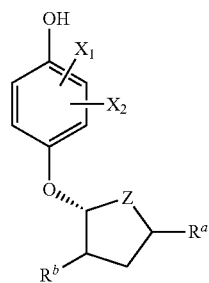

I-d or a pharmaceutically acceptable salt thereof, wherein Z, $X_1$ and $X_2$ are as defined and described above and herein, and $R^a$ and $R^b$ are each independently selected from the group consisting of hydrogen, optionally substituted C1-6 aliphatic, and —OR$^2$, wherein R$^2$ is selected from the group consisting of hydrogen and optionally substituted C1-6 aliphatic.

In some embodiments, Z is O. In some embodiments, Z is S. In some embodiments, Z is SO. In some embodiments, Z is SO$_2$. In some embodiments, each of R$^a$ and R$^b$ is hydrogen. In some embodiments, R$^a$ is optionally substituted C1-6 aliphatic, e.g., methyl or —CH$_2$OH. In some embodiments, R$^b$ is —OR$^2$ (e.g., —OH). In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —OR$^2$, —SR$^2$, —N(R$^2$)$_2$, —COOR$^2$, and —CON(R$^2$)$_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In some embodiments, the present invention provides a compound of formula I-d, substantially free of a compound of formula II-d.

In some embodiments, the present invention provides a compound of formula I-e:

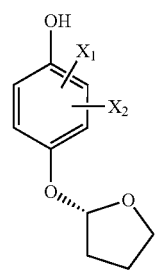

I-e or a pharmaceutically acceptable salt thereof, wherein $X_1$ and $X_2$ are as defined and described above and herein.

In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —OR$^2$, —SR$^2$, —N(R$^2$)$_2$, —COOR$^2$, and —CON(R$^2$)$_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In some embodiments, the present invention provides a compound of formula I-e, substantially free of a compound of formula II-e.

In some embodiments, the present invention provides a compound of formula I-f:

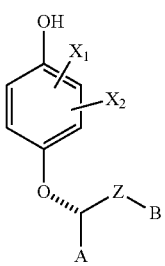

I-f or a pharmaceutically acceptable salt thereof, wherein:
Z is selected from NR$_1$, S, O, SO and SO$_2$;
R$_1$ is selected from hydrogen and C1-6 aliphatic;

X₁ and X₂ are independently selected from hydrogen, halogen, cyano, nitro, optionally substituted C1-6 aliphatic, —OR², —SR², —N(R²)₂, —COOR², and —CON(R²)₂;

each R² is independently hydrogen or an optionally substituted C1-6 aliphatic; and A and B are independently an optionally substituted group selected from the group consisting of: C1-6 aliphatic; a 3-8 membered saturated carbocyclic ring; and phenyl.

In some embodiments, Z is O. In some embodiments, each of X₁ and X₂ is hydrogen. In other embodiments, one of X₁ and X₂ is hydrogen and the other is halogen, cyano, nitro, optionally substituted C1-6 aliphatic, —OR², —SR², —N(R²)₂, —COOR², and —CON(R²)₂. In some embodiments, one of X₁ and X₂ is hydrogen and the other is halogen. In some embodiments, one of X₁ and X₂ is hydrogen and the other is fluoro or chloro. In some embodiments, one of X₁ and X₂ is hydrogen and the other is nitro. In some embodiments, one of X₁ and X₂ is hydrogen and the other is C1-6 aliphatic. In some embodiments, one of X₁ and X₂ is hydrogen and the other is methyl. In some embodiments, A is C1-6 aliphatic. In some embodiments, A is methyl or ethyl. In some embodiments, A is a 3-8 membered saturated carbocyclic ring. In some embodiments, A is cyclohexyl. In some embodiments, A is phenyl. In some embodiments, B is C1-6 aliphatic. In some embodiments, B is ethyl or n-propyl. In some embodiments, B is a 3-8 membered saturated carbocyclic ring. In some embodiments, B is cyclopentyl.

In some embodiments, the present invention provides a compound of formula I-f, substantially free of a compound of formula II-f.

In some embodiments, the present invention provides a compound of formula II-a:

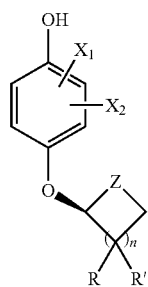

II-a or a pharmaceutically acceptable salt thereof, wherein Z, X₁ and X₂ are as defined and described above and herein, n is 1, 2, 3, 4 or 5, each R is independently selected from hydrogen and C1-6 aliphatic, and each R' is independently selected from hydrogen, C1-6 aliphatic and —OR^a, wherein each R^a is independently selected from hydrogen and C1-6 aliphatic.

In some embodiments, n is 2, 3 or 4. In some embodiments, n is 2 or 3. In some embodiments, each occurrence of R and R' is hydrogen. In some embodiments, at least one occurrence of R' is —OR^a, wherein R^a is hydrogen or C1-6 aliphatic (e.g., methyl). In some embodiments, In some embodiments, Z is O. In some embodiments, Z is S. In some embodiments, Z is SO. In some embodiments, Z is SO₂. In some embodiments, each of X₁ and X₂ is hydrogen. In other embodiments, one of X₁ and X₂ is hydrogen and the other is halogen, cyano, nitro, optionally substituted C1-6 aliphatic, —OR², —SR², —N(R²)₂, —COOR², and —CON(R²)₂. In some embodiments, one of X₁ and X₂ is hydrogen and the other is halogen. In some embodiments, one of X₁ and X₂ is hydrogen and the other is fluoro or chloro. In some embodiments, one of X₁ and X₂ is hydrogen and the other is C1-6 aliphatic. In some embodiments, one of X₁ and X₂ is hydrogen and the other is methyl.

In some embodiments, the present invention provides a compound of formula II-a, substantially free of a compound of formula I-a.

In some embodiments, the present invention provides a compound of formula II-b:

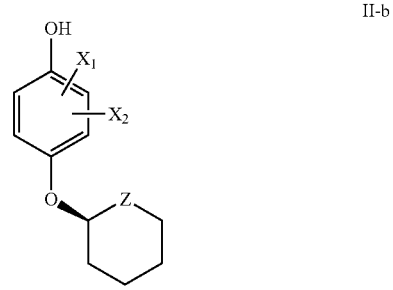

II-b or a pharmaceutically acceptable salt thereof, wherein Z, X₁ and X₂ are as defined and described above and herein.

In some embodiments, Z is O. In some embodiments, Z is S. In some embodiments, each of X₁ and X₂ is hydrogen. In other embodiments, one of X₁ and X₂ is hydrogen and the other is halogen, cyano, nitro, optionally substituted C1-6 aliphatic, —OR², —SR², —N(R²)₂, —COOR², and —CON(R²)₂. In some embodiments, one of X₁ and X₂ is hydrogen and the other is halogen. In some embodiments, one of X₁ and X₂ is hydrogen and the other is fluoro or chloro. In some embodiments, one of X₁ and X₂ is hydrogen and the other is C1-6 aliphatic. In some embodiments, one of X₁ and X₂ is hydrogen and the other is methyl.

In some embodiments, the present invention provides a compound of formula II-b, substantially free of a compound of formula I-b.

In some embodiments, the present invention provides a compound of formula II-c:

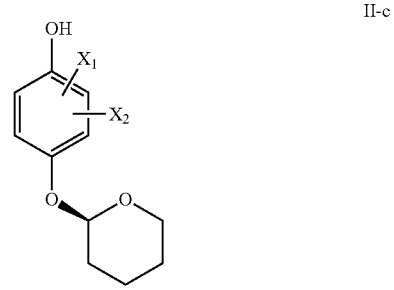

II-c or a pharmaceutically acceptable salt thereof, wherein X₁ and X₂ are as defined and described above and herein.

In some embodiments, each of X₁ and X₂ is hydrogen. In other embodiments, one of X₁ and X₂ is hydrogen and the other is halogen, cyano, nitro, optionally substituted C1-6 aliphatic, —OR², —SR², —N(R²)₂, —COOR², and —CON(R²)₂. In some embodiments, one of X₁ and X₂ is hydrogen and the other is halogen. In some embodiments, one of X₁ and X₂ is hydrogen and the other is fluoro or chloro. In some embodiments, one of X₁ and X₂ is hydrogen and the other is C1-6 aliphatic. In some embodiments, one of X₁ and X₂ is hydrogen and the other is methyl.

In some embodiments, the present invention provides a compound of formula II-c, substantially free of a compound of formula I-c.

In some embodiments, the present invention provides a compound of formula II-d:

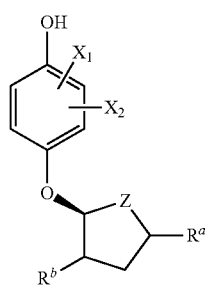

II-d or a pharmaceutically acceptable salt thereof, wherein Z, $X_1$ and $X_2$ are as defined and described above and herein, and $R^a$ and $R^b$ are each independently selected from the group consisting of hydrogen, optionally substituted C1-6 aliphatic, and —$OR^2$, wherein $R^2$ is selected from the group consisting of hydrogen and optionally substituted C1-6 aliphatic.

In some embodiments, Z is O. In some embodiments, Z is S. In some embodiments, Z is SO. In some embodiments, Z is $SO_2$. In some embodiments, each of $R^a$ and $R^b$ is hydrogen. In some embodiments, $R^a$ is optionally substituted C1-6 aliphatic, e.g., methyl or —$CH_2OH$. In some embodiments, $R^b$ is —$OR^2$ (e.g., —OH). In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —$OR^2$, —$SR^2$, —$N(R^2)_2$, —$COOR^2$, and —$CON(R^2)_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In some embodiments, the present invention provides a compound of formula II-d, substantially free of a compound of formula I-d.

In some embodiments, the present invention provides a compound of formula II-e:

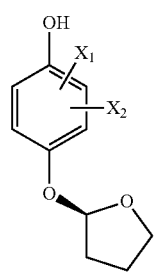

II-e or a pharmaceutically acceptable salt thereof, wherein $X_1$ and $X_2$ are as defined and described above and herein.

In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —$OR^2$, —$SR^2$, —$N(R^2)_2$, —$COOR^2$, and —$CON(R^2)_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is C1-6 aliphatic. In some embodiments, one of $X_1$ and $X_2$ is hydrogen and the other is methyl.

In some embodiments, the present invention provides a compound of formula II-e, substantially free of a compound of formula I-e.

In some embodiments, the present invention provides a compound of formula II-f:

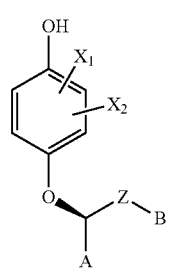

II-f or a pharmaceutically acceptable salt thereof, wherein:

Z is selected from $NR_1$, S, O, SO and $SO_2$;

$R_1$ is selected from hydrogen and C1-6 aliphatic;

$X_1$ and $X_2$ are independently selected from hydrogen, halogen, cyano, nitro, optionally substituted C1-6 aliphatic, —$OR^2$, —$SR^2$, —$N(R^2)_2$, —$COOR^2$, and —$CON(R^2)_2$;

each $R^2$ is independently hydrogen or an optionally substituted C1-6 aliphatic; and A and B are independently an optionally substituted group selected from the group consisting of: C1-6 aliphatic; a 3-8 membered saturated carbocyclic ring; and phenyl.

In some embodiments, Z is O. In some embodiments, each of $X_1$ and $X_2$ is hydrogen. In other embodiments, one of $X_1$ and $X_2$ is hydrogen and the other is halogen, cyano, nitro, optionally substituted C1-6 aliphatic, —$OR^2$, —$SR^2$, —$N(R^2)_2$, —$COOR^2$, and —$CON(R^2)_2$. In some embodiments, one of $X_1$ and $X_2$ is hydrogen and the other is halogen. In some embodiments, one of $X_1$ and $X_2$ is hydrogen and the other is fluoro or chloro. In some embodiments, one of $X_1$ and $X_2$ is hydrogen and the other is nitro. In some embodiments, one of $X_1$ and $X_2$ is hydrogen and the other is C1-6 aliphatic. In some embodiments, one of $X_1$ and $X_2$ is hydrogen and the other is methyl. In some embodiments, A is C1-6 aliphatic. In some embodiments, A is methyl or ethyl. In some embodiments, A is a 3-8 membered saturated carbocyclic ring. In some embodiments, A is cyclohexyl. In some embodiments, A is phenyl. In some embodiments, B is C1-6 aliphatic. In some embodiments, B is ethyl or n-propyl. In some embodiments, B is a 3-8 membered saturated carbocyclic ring. In some embodiments, B is cyclopentyl.

In some embodiments, the present invention provides a compound of formula II-f, substantially free of a compound of formula I-f.

Representative Examples of Chiral Non-Racemic Compounds

There exists an abundance of compounds useful herein that are encompassed by the general formula set forth above in relation to the present chiral non-racemic compounds. While an exhaustive list of every compound falling within the general formula set forth above is not provided, the below-listed compounds are intended to serve as exemplary, non-limiting representative structures of the compounds that are particularly desired for use in the present disclosure.

Examples: Cyclic deoxyArbutins

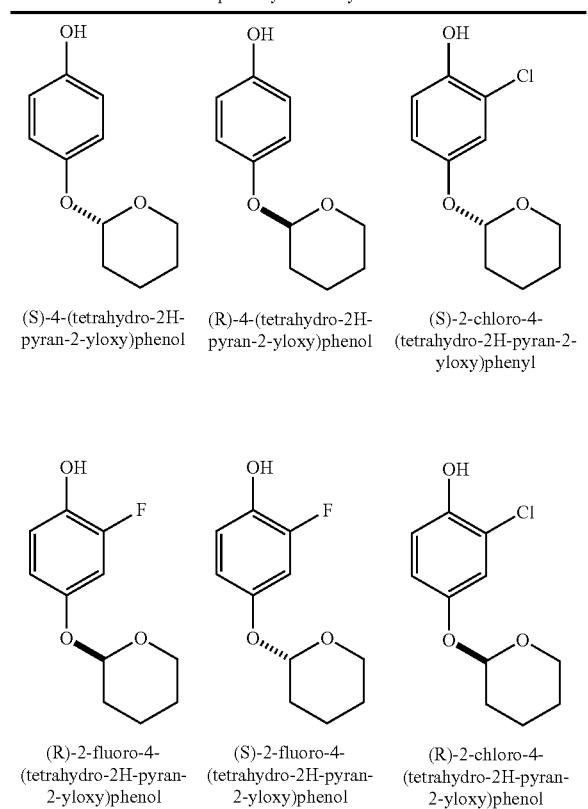

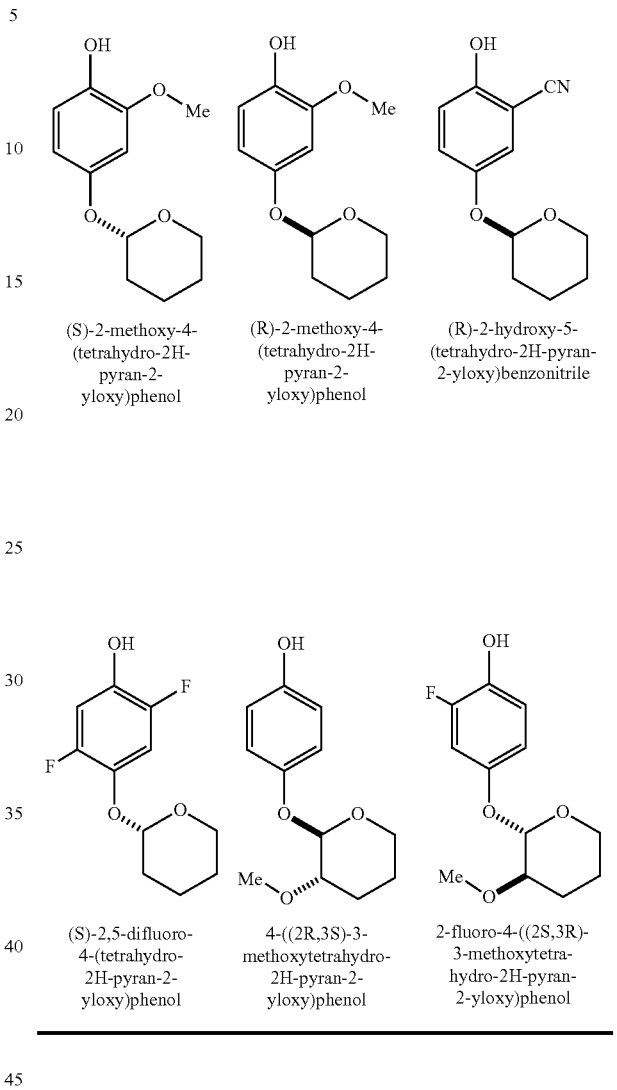

Examples: Other ring sizes

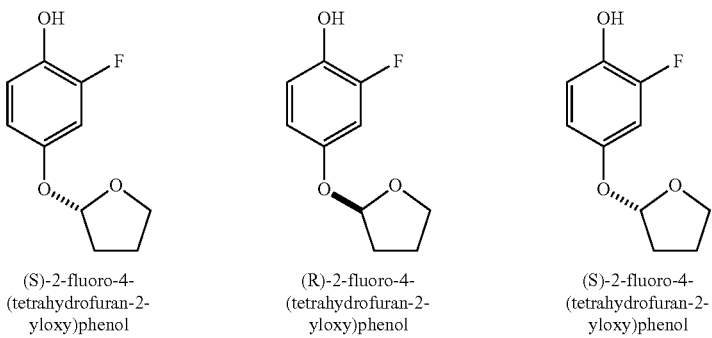

Examples: Other ring sizes

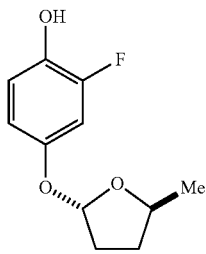

2-fluoro-4-((2S,5S)-5-methyltetrahydrofuran-2-yloxy)phenol

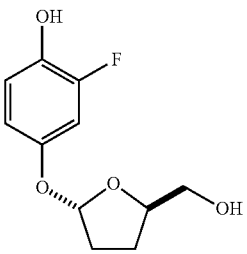

2-fluoro-4-((2S,5R)-5-(hydroxymethyl)tetrahydrofuran-2-yloxy)phenol

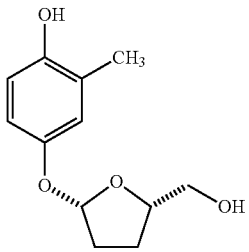

4-((2S,5S)-5-(hydroxymethyl)tetrahydrofuran-2-yloxy)-2-methylphenol

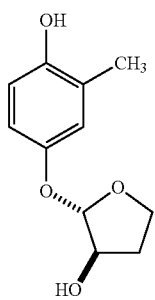

(2S,3R)-2-(4-hydroxy-3-methylphenoxy)tetrahydrofuran-3-ol

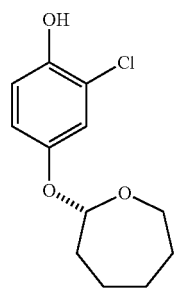

(S)-2-chloro-4-(oxepan-2-yloxy)phenol

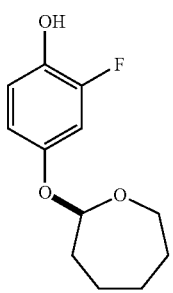

(R)-2-fluoro-4-(oxepan-2-yloxy)phenol

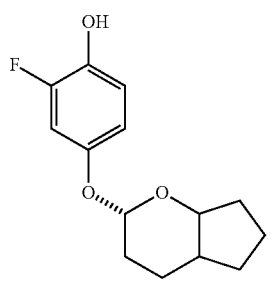

2-fluoro-4-((2S)-octahydrocyclopenta[b]pyran-2-yloxy)phenol

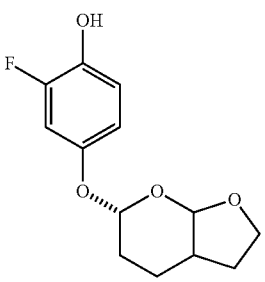

2-fluoro-4-((6R)-hexahydro-2H-furo[2,3-b]pyran-6-yloxy)phenol

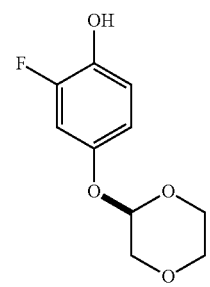

(R)-4-(1,4-dioxan-2-yloxy)-2-fluorophenol

(R)-2-fluoro-4-(oxocan-2-yloxy)phenol

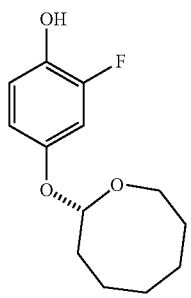

(S)-2-fluoro-4-(oxocan-2-yloxy)phenol

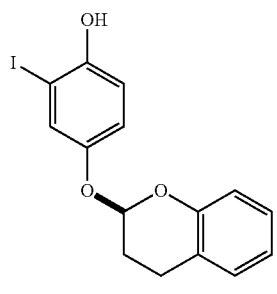

(S)-4-(chroman-2-yloxy)-2-iodophenol

Examples: Other ring sizes

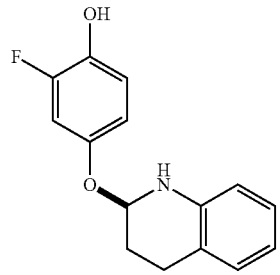

(R)-2-fluoro-4-(1,2,3,4-tetra-hydroquinolin-2-yloxy)phenol

Examples: ThiodeoxyArbutins

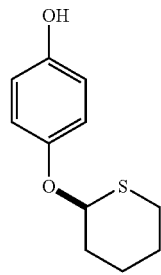

(S)-4-(tetrahydro-2H-thiopyran-2-yloxy)phenol

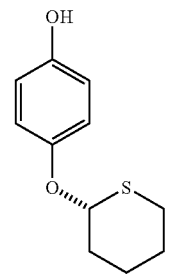

(R)-4-(tetrahydro-2H-thiopyran-2-yloxy)phenol

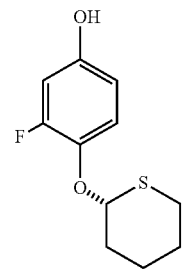

(R)-3-fluoro-4-(tetrahydro-2H-thiopyran-2-yloxy)phenol

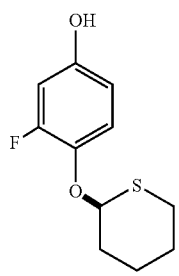

(S)-3-fluoro-4-(tetrahydro-2H-thiopyran-2-yloxy)phenol

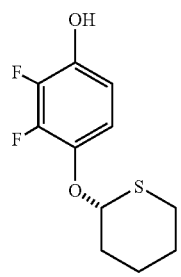

(R)-2,3-difluoro-4-(tetrahydro-2H-thiopyran-2-yloxy)phenol

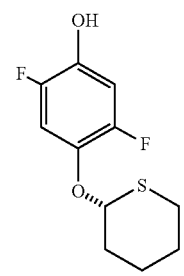

(R)-2,5-difluoro-4-(tetrahydro-2H-thiopyran-2-yloxy)phenol

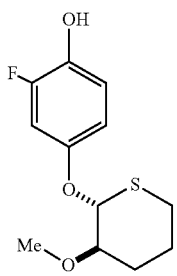

2-fluoro-4-((2R,3R)-3-methoxytetra-hydro-2H-thiopyran-2-yloxy)phenol

Examples: Other Thio analogs

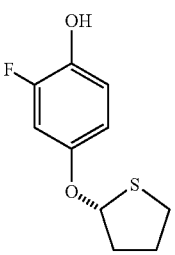

(R)-2-fluoro-4-(tetrahydro-thiophen-2-yloxy)phenol

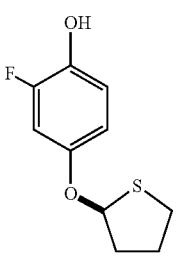

(S)-2-fluoro-4-(tetrahydro-thiophen-2-yloxy)phenol

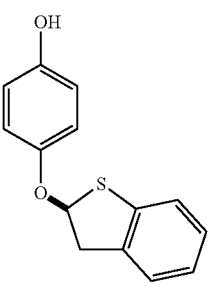

(S)-4-(2,3-dihydro-benzo[b]thiophen-2-yloxy)phenol

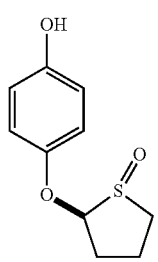

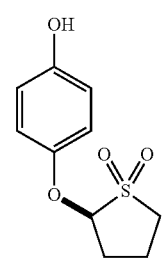

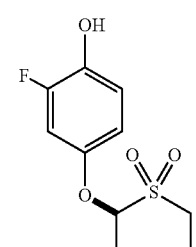

Examples: Brominated analogs
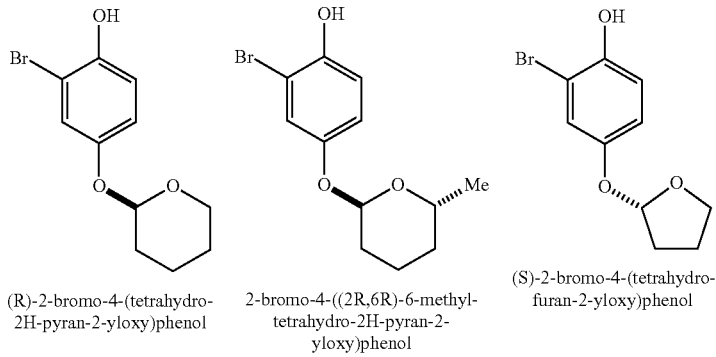
Examples: Acyclic Analogs
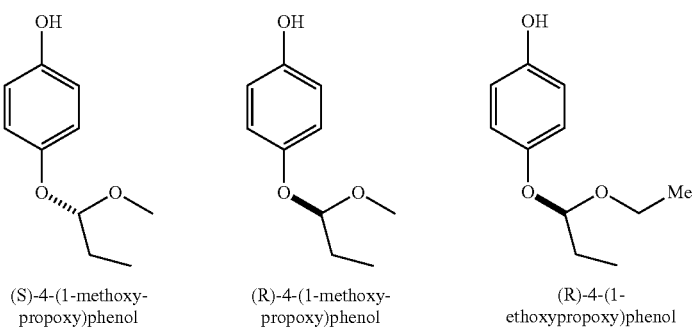
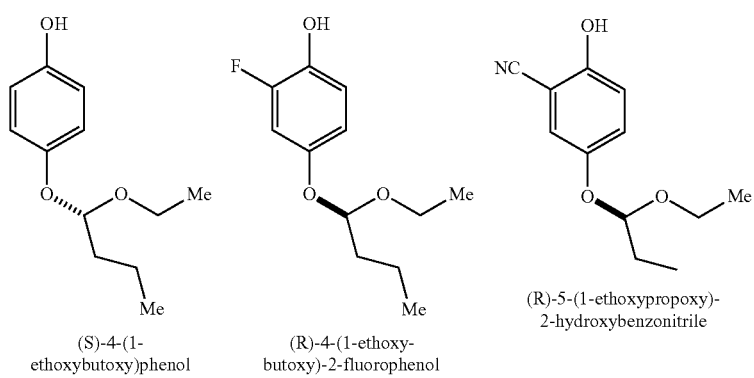

Examples: Other Acyclic Analogs

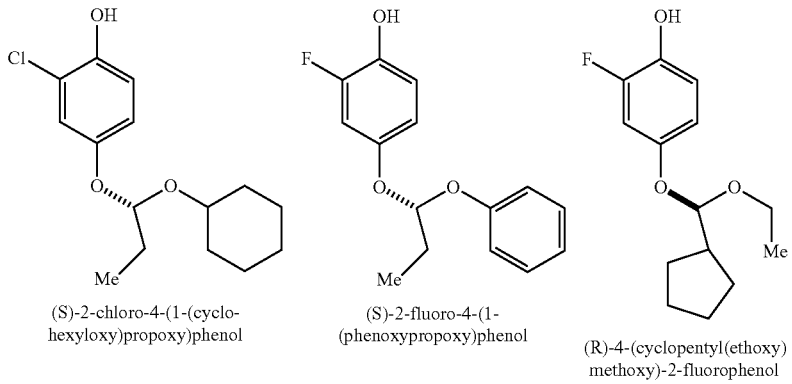

| Examples: Other Acyclic Analogs | | |
|---|---|---|
| (S)-2-chloro-4-(1-(cyclo-hexyloxy)propoxy)phenol | (S)-2-fluoro-4-(1-(phenoxypropoxy)phenol | (R)-4-(cyclopentyl(ethoxy)methoxy)-2-fluorophenol |

To achieve significant skin penetration, compounds described herein may have an appropriate hydrophilicity/hydrophobicity ratio. Some compounds, such as the naturally-occurring alpha and beta arbutins, have sugar moieties as part of their structure. This may render them too hydrophilic to be useful topical agents. Accordingly, in some embodiments of the compounds disclosed herein, the ratio of carbon atoms to oxygen atoms in the side chain may be at least 2:1. (The ratio in both alpha and beta arbutin is 6:5, which is only ~1:1) and preferable 3:1 or greater, and more preferably 4:1 or greater. For (+) deoxyarbutin, for example, the ratio is 5:1 in the side chain (one oxygen atom and 5 carbon atoms in the ring. Note that the oxygen atom that connects the side chain to the benzene ring is NOT included in this ratio).

Compounds described herein may not include naturally-occurring alpha-arbutin. When natural products such as alpha-arbutin are applied to the skin, enzymes naturally present in the skin may break these compounds down. While alpha-arbutin may undergo such degradation, deoxyArbutin and other compounds described herein may be significantly more stable under enzymatic hydrolysis conditions.

Salts, Isomers, Protected Forms, and Prodrugs

Unless otherwise specified, a reference to a particular compound also includes ionic, salt, solvate, and protected forms of thereof, for example, as discussed below. It may be convenient or desirable to prepare, purify, and/or handle a corresponding salt of the active compound, for example, a pharmaceutically-acceptable salt. Examples of pharmaceutically acceptable salts are discussed in Berge et al., *J. Pharm. Sci.*, 66, 1-19 (1977). Exemplary pharmaceutically acceptable salts include hydrochloride salts.

For example, if the compound is anionic, or has a functional group which may be anionic (e.g., —COOH may be —COO—), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., $—NH_2$ may be $—NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, $—OCH_3$, is not to be construed as a reference to its structural isomer, a hydroxymethyl group, $—CH_2OH$. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and paramethoxyphenyl).

Note that specifically included in the term "isomer" are compounds with one or more isotopic substitutions. For example, H may be in any isotopic form, including $^1H$, $^2H(D)$, and $^3H(T)$; C may be in any isotopic form, including $^{12}C$, $^{13}C$, and $^{14}C$; O may be in any isotopic form, including $^{16}O$ and $^{18}O$; and the like.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1999).

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc). For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. For example, an amine group may be protected, for example, as an amide or a urethane, for example, as: a methyl amide (—NHCO—CH3); a benzyloxy amide (—NHCO—OCH$_2$C$_6$H$_5$, —NHCbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide.

For example, a carboxylic acid group may be protected as an ester for example, as: an C$_{1-7}$ alkyl ester (e.g. a methyl ester; a t-butyl ester); a C$_{1-7}$ haloalkyl ester (e.g., a C$_{1-7}$ trihaloalkylester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$). It may be convenient or desirable to prepare, purify, and/or handle the active compound in the form of a prodrug.

The term "prodrug", as used herein, pertains to a compound which, when metabolized (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C$_{1-7}$ alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexylcarbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Compositions of Actives

Combinations which may be particularly effective are shown in the table below. Each composition includes two components; component A is the (−) enantiomer of deoxyArbutin (4-(tetrahydro-2H-pyran-2-yloxy)phenol), while component B is a second deoxyArbutin compound as indicated below.

| Composition | Component A | Component B |
|---|---|---|
| Alpha-1 | 0.1-5% (−) deoxyArbutin | 0.1-3% (−) 2-fluoro deoxyArbutin (2-fluoro-4-(tetrahydro-2H-pyran-2-yloxy)phenol) |
| Beta-1 | 0.1-5% (−) deoxyArbutin | 0.1-3% (−) 2-chloro deoxyArbutin (2-chloro-4-(tetrahydro-2H-pyran-2-yloxy)phenol) |
| Gamma-1 | 0.1-5% (−) deoxyArbutin | 0.1-3% (−) 2,5-dichloro deoxyArbutin (2,5-dichloro-4-(tetrahydro-2H-pyran-2-yloxy)phenol) |
| Delta-1 | 0.1-5% (−) deoxyArbutin | 0.1-3% thio-deoxyArbutin (4-(tetrahydro-2H-thiopyran-2-yloxy)phenol) |
| Alpha-2 | 0.1-5% (−) deoxyArbutin | 0.1-5% 2-fluoro-thio-deoxyArbutin (2-fluoro-4-(tetrahydro-2H-thiopyran-2-yloxy)phenol) |

Methods of Separating (−) from (+) Enantiomers.

Many methods of chiral separation exist in the art, yet none have been applied to the separation of compounds that have a single chiral center in an acetal or ketal linkage, and no other chiral moiety. For example, there are many examples of molecules containing a tetrahydropyranyl moiety, but no examples where, when the chiral center of the tetrahydropyran is the only chiral center, a chiral separation has been successfully performed. Indeed, the failure of the ChiralPak IA, 4.6×250 mm (Diacel Chemical Ind., Ltd.) method of separation teaches that such compounds are not amenable to separation, and the temporal nature of the THP group; its main use as a temporary, or protecting group, has resulted in either a lack of interest or lack of progress in this area. For example, the art describes the reaction of (−) and (+) glycidol with dihydropyran in WO2010027113A2: Process for Preparing (S)-(−)-Felodipine, but the resulting tetrahydropyran is not the object of the separation, nor does it materially participate in the chemistry. U.S. Pat. No. 7,393,858 describes tetrahydropyran compounds as tachykinin antagonists, but here again the chiral center of the instant disclosure is not the method by which the enantiomers are separated.

Even synthesis patents directed at the deoxyArbutin class itself, for example Kleinebekel's US20090216002A1: Synthesis of Hydroquinone Derivatives, claiming improved methods for the syntheses of these molecules, no mention is made of chiral synthesis, separation, or even the fact that a chiral center exists. Again, U.S. Pat. No. 5,585,525 specifically mentions this class of compounds, with no mention of any chiral separation.

Products and Formulations Incorporating the Present Compounds

In another aspect, products and formulations that comprise the chiral non-racemic compounds are provided, as well as combinations of such products and formulations. Indeed, the combined and systematic use of products and formulations containing the compounds of the present disclosure serve to beautify and improve the condition of the mammalian skin, and particularly human skin, to which they are applied. These products and formulations may take a variety of shapes and forms, depending on the specific needs and/or abilities of the practitioner, as well as the purpose for which their employment is sought. The use of the compounds and products incorporating same may result in a marked reduction in the appearance of pigment, as well as an improvement in the overall appearance of mammalian, and particularly human, skin.

Compositions incorporating the present compounds may be prepared as described in a copending provisional patent application 61/583,247 entitled "SKIN LIGHTENING COMPOSITIONS" filed on Jan. 5, 2012.

According to another embodiment, the invention provides a composition comprising a compound of this invention or a pharmaceutically acceptable derivative thereof and a pharmaceutically acceptable carrier, adjuvant, or vehicle.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Personal Care Products

Thus, personal care products comprising the chiral, non-racemic compounds of the present disclosure are disclosed. Suitable personal care products comprising the present compounds, include, but are not limited to: hand soaps, hand sanitizers, body washes, mouth washes, toothpastes, shower gels, shampoos, body lotions, facial moisturizers and other facial treatment products, eye creams, deodorants and combinations thereof. The personal care products disclosed herein take the form of a wipe product, particularly suitable for wiping or drying the face or hands. In such instances, the chiral, non-racemic compounds of the present disclosure may be embedded or impregnated into said wipe product. In yet still another embodiment, the personal care product disclosed herein takes the form of a tissue or towel, also suitable for wiping or drying the face or hands. In another embodiment, the personal care product takes the form of a first aid antiseptic for hyperpigmented, burned, or acne-affected skin and/or for pre or post surgical use. In another embodiment, the personal care product takes the form of a bandage.

Skin Care Products

The chiral, non-racemic compounds of the present disclosure may also be incorporated into a skin care product. In one embodiment, the skin care product incorporates a dermatologically acceptable carrier to facilitate safe transfer of the present compounds to a desired area of mammalian skin. The skin care product of the present disclosure may comprise certain adjunct ingredients. Said adjuncts include, but are not limited to: antimicrobial and antifungal actives, surfactants, desquamation actives, anti-acne actives, anti-wrinkle actives, anti-atrophy actives, anti-oxidants, radical scavengers, chelators, flavonoids, anti-inflammatory agents, anti-cellulite agents, topical anesthetics, tanning actives, sunscreen actives, conditioning agents, thickening agents, detackifying agents, odor control agents, skin sensates, antiperspirants and mixtures thereof. Indeed, a complete description and examples of each of the aforementioned adjunct ingredients is set forth in U.S. Pat. No. 6,294,186, assigned to The Procter and Gamble Company, Cincinnati, Ohio and incorporated herein by reference.

Topical Formulations Comprising Present Compounds

The chiral, non-racemic compounds disclosed herein may also be formulated into compositions for topical application onto mammalian, and particularly human, skin. In one embodiment, the topical formulations disclosed herein include a safe and effective amount of pigment inhibiting agents and other ingredients that are adapted to enhance the appearance of the mammalian skin onto which they are applied.

By "safe and effective amount", it is intended that an incorporated amount of a compound or composition be high enough to significantly improve the appearance of the skin, but low enough to discourage side effects, which may eventually reduce the appearance and beauty of the skin. Indeed, the safe and effective amount of an agent for use in the compounds and/or compositions of the present disclosure will vary depending on one or more of the following factors: the nature of the skin for which treatment is sought, the age and physical condition of the skin for which treatment is sought, the severity of any existing skin conditions, the intended duration of the treatment, the existence and nature of any concurrent therapy, the particular agent for which employment is sought, the particular excipients utilized, and the needs and/or abilities of the formulator of the present compounds and compositions. Nevertheless, the appropriate amount of the agent, such as one or more chiral non-racemic compounds disclosed herein, to be incorporated into the present compositions may be determined by routine experimentation with animal models. Indeed, one such model includes, but is not limited to, pigmented *Cavia porcellus* models of mammalian, and particularly human, skin.

The chiral non-racemic compounds of the present disclosure may be administered systemically, e.g., by subcutaneous or injection, but typically and especially transdermally. The chiral non-racemic compounds disclosed herein may be applied directly to the mammalian skin for which treatment is sought in a unit dosage form. As discussed in the "Formulations" section of the present disclosure, the precise amount of the present compounds incorporated into a unit dosage form will depend upon one or more factors disclosed hereinbefore, and particularly the needs and/or abilities of the formulator of the present compositions and the nature of the mammalian skin for which treatment is desired.

The alternate dose forms for use with the present compounds and compositions include nasal, transdermal, rectal, sublingual, oral and combinations thereof. One or more carriers suitable for use with the present compounds may be employed to achieve delivery of the compounds and compositions, and particularly for injection or surgical implants. Said carriers include, but are not limited to: hydrogels, controlled release or sustained release devices, polylactic acid, collagen matrices, and combinations thereof. Implant devices that are coated with the chiral, non-racemic compounds and/or formulations are disclosed herein. The compounds and/or formulations disclosed herein may also be dissolved in a buffer and mixed with a collagen gel for coating onto the porous end of an implant device.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Oral forms suitable for administration of the present compounds and formulations include, but are not limited to: liposomes, lipid emulsions, proteinaceous cages, other excipients and combinations thereof. Use of the term "excipients" herein is intended to encompass any physiologically inert, pharmacologically inactive material known to those of ordinary skill in the art. Suitable excipients for use in the present disclosure are compatible with the physical and chemical characteristics of the particular differentiation-promoting ingredient for which employment is sought, as well as the mammalian skin substrate for which application is desired. Suitable excipients for use herein include but are not limited to polymers, resins, plasticizers, fillers, lubricants, binders, disintegrants, solvents, co-solvents, buffer systems, surfactants, preservatives, sweetening agents, flavoring agents, fragrance agents pharmaceutical grade dyes, pigments and combinations thereof.

When the use of a flavoring agent excipient in the compositions of the present disclosure is desired, suitable such agents may be selected from those described in *Remington's Pharmaceutical Sciences*, 18th Edition, Mack Publishing Company, 1990, pp. 1288-1300, incorporated by reference herein. Dyes or pigments include but are not limited to those described in *Handbook of Pharmaceutical Excipients*, Second Edition pp. 126-134, 1994 by the American Pharmaceutical Association & the Pharmaceutical Press, incorporated by reference herein.

Suitable solvents and co-solvents include but are not limited to water, ethanol, glycerin, propylene glycol, polyethylene glycol and combinations thereof. Suitable buffer systems for use as excipients herein include, but are not limited to potassium acetate, boric carbonic, phosphoric, succinic, malic, tartaric, citric, acetic, benzoic, lactic, glyceric, gluconic, glutaric, glutamic and combinations thereof. Suitable buffer systems for use with the compounds disclosed herein are phosphoric, tartaric, citric, and potassium acetate.

Suitable surfactants for use as excipients include but are not limited to polyoxyethylene sorbitan fatty acid esters, polyoxyethylene monoalkyl ethers, sucrose monoesters and lanolin esters, ethers and mixtures thereof. Moreover, suitable preservatives for use as excipients of the present disclosure include, but are not limited to, phenol, alkyl esters of parahydroxybenzoic acid, benzoic acid and the salts thereof, boric acid and the thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Suitable excipients are the salts of benzoic acid, cetylpyridinium chloride, phenoxyethanol, succinate, methyl paraben, propyl paraben and combinations thereof.

Suitable sweeteners for use with the compounds disclosed herein include, but are not limited to, sucrose, glucose, saccharin, aspartame and combinations thereof. Sucrose, saccharin and combinations thereof are suitable sweeteners for use with the present compounds. Binders for use in conjunction with the present compounds include but are not limited to methylcellulose, sodium carboxymethylcellulose, hydroxypropylmethylcellulose, carbomer, prodione, acacia, guar gum, xanthan gum, tragcanth and combinations thereof. Particularly suitable binders for use with the compounds disclosed herein include, but are not limited to, methylcellulose, carbomer, xanthan gum, guar gum, povidone and combinations thereof.

Suitable fillers for use with the chiral, non-racemic compounds disclosed herein include but are not limited to lactose, sucrose, maltodextrin, mannitol, starch, microcrystalline cellulose and combinations thereof. Suitable plasticizers for use with the present compounds include, but are not limited to polyethylene glycol, propylene glycol, dibutylphthalate, and castor oil, acetylated monoglycerides, triactin and combinations thereof. Suitable lubricants for use with the compounds disclosed herein include, but are not limited to, magnesium stearate, stearic acid, talc and combinations thereof. Suitable disintegrants for use with the compounds disclosed herein, but are not limited to, crospovidone, sodium carboxymethyl starch, sodium starch glycollate, sodium carboxymethyl cellulose, alginic acid, clays, ion exchange resins and combinations thereof. Suitable polymers for use as excipients include, but are not limited to, hydroxypropylmethylcellulose (HPMC), hydroxypropylcellulose (HPC), carboxymethylcellulose, acrylic resins such as Eudragit® RL30D, methylcellulose, ethylcellulose, polyvinylpyrrolidone, commercially available film-coating preparations such as Dri-Klear, Opadry® and combinations thereof. The precise ingredients and suitable excipients for use with the compounds of the present disclosure will depend on several factors, and particularly the needs and/or abilities of the formulator and the nature of the skin for which treatment with the present compounds is desired. Nevertheless, the above discussion is intended only to serve as a guide to a person of ordinary skill in the art. Certainly, compounds analogous or similar to those listed above will also be suitable for employment with the compounds of the present disclosure.

Articles of Manufacture & Kits

Moreover, articles of manufacture comprising the chiral non-racemic compounds of the present disclosure and/or one or more of the aforementioned products, may be used for personal care, skin care and medical applications. One or more products as described hereinbefore may be packaged in a container or dispenser with a set of instructions for the consumer. An article of manufacture may comprise (a) container or dispenser, (b) product and (c) set of instructions to apply said product to an appropriate substrate to convey beautification and improvement benefits to mammalian skin. Containers and/or dispensers suitable for the article of manufacture may include but are not limited to air-tight sealed aluminum pouches, sachets and bags, PET bottles and tubes, flow-wrap pouches, foaming dispensers, spray dispensers and combinations thereof. The article of manufacture may further comprise a set of instructions in association with the container. By "in association with," it is meant that the instructions are either directly printed on the container or dispenser itself or presented in a different fashion including, but not limited to: a brochure, print advertisement, electronic advertisement and/or verbal communication, so as to communicate the set of the instructions to a consumer of the article of manufacture.

The set of instructions typically relate to the use of the product to apply the chiral non-racemic compounds of the present disclosure onto a suitable substrate for which treatment is sought. The set of instructions may further comprise the instruction to allow the present compounds to remain on the treated substrate, without rinsing or otherwise removing the compounds from the treated substrate. Nevertheless, the precise instructions included with the article of manufacture will depend on the precise compounds and the product for which the inclusion of instructions is desired and the substrate onto which application of the product is intended. The instructions included in the present articles of manufacture may coincide with the methods set forth in the "Methods of Use" section of the present disclosure.

Methods of Using the Present Compounds and Products

Methods of using the chiral non-racemic compounds discussed herein are also disclosed herein. The compositions and products of the present disclosure are suitable for a variety of uses. Suitable uses of the present compositions include, but are not limited to, methods of beautifying mammalian skin, methods of lightening mammalian skin, methods of reducing the appearance of blemishes on mammalian skin, methods of slowing the deterioration of mammalian skin, methods of reducing the loss of function of mammalian skin, and methods of reducing pigmentation of mammalian skin. Each of the above methods comprises topically applying a chiral, non-racemic compound as described above and herein (e.g., a compound of formula I or formula II) to an area in need of treatment.

The methods may comprise topically applying a composition or product comprising the same to mammalian, and particularly human, skin for which treatment is desired. Examples of areas and/or surfaces in need of treatment, against which the compounds and compositions of the present disclosure are effective include, but are not limited to: the face, the neck, décolletage, hands, the nose, the nasal canal or passage, an article of clothing, hyperpigmented, acne-affected, or burned skin, pre or post surgical areas and combinations thereof.

The compounds of the present disclosure are useful in providing actual and significant beautification and improvement benefits to mammalian, and particularly human, skin. The chiral non-racemic compounds and compositions disclosed herein may serve to increase the appeal of the mammalian skin to which they are applied, while maintaining a youthful appearance thereof. Further and compelling, the compounds and products of the present disclosure may discourage the onset of physical ailments resulting from existing skin conditions and minimize irritation to mammalian skin following application of the present compounds. In an embodiment, the compounds, compositions and products disclosed herein are useful for employment in cosmetics, creams and oils, and in compositions for the treatment of various skin dysfunctions. Exemplary skin disorders include but are not limited to conditions such as melasma, chloasma, pigmented spots, lentigo senilis, freckles, café au lait spots, liver spots, pigmented keratosis, ephelides, post-inflammatory or post surgical hyperpigmentation, periorbital darkening, mottling, and solar lentigens.

The compounds and/or products disclosed herein may be directly applied to the mammalian skin for which treatment is desired. The compounds and/or products disclosed herein may be applied transdermally to the mammalian skin for which treatment is sought. The exact amount of the compounds will depend upon the needs and abilities of the formulator and practitioner of the present methods. The compounds of the present disclosure may be conveyed to the mammalian skin for which treatment is desired in an amount of from about 0.001% to about 40% of a lotion or cream, suitably from about 0.01% to about 10% at least once per day. Once applied, the compositions are rubbed on the treated surfaces for a period of time to ensure coverage. In another embodiment, transdermal dosages may be designed and intended to attain minimal serum or plasma levels, based upon techniques known to those skilled in the art of pharmacokinetics and formulations.

Methods for lightening mammalian skin may comprise the administration of a therapeutically effective amount of a compound or product to the skin or regions of the skin to be lightened. The amount of active agent and frequency of application will vary widely depending upon the pigmentation already in existence, the rate of further darkening of the skin or region of the skin, and the level of lightening desired. Additionally, when the product is used to treat hyperpigmented spots, it is expected that the application and amount will differ from the amount for lightening of general skin tone.

Any dose that is safe and effective may be used, and accordingly it is contemplated that for certain dosage forms, particularly topical dosage forms, the "dose" is any amount that provides the desired effect.

A therapeutically effective amount of skin lightening agent in a topical composition is applied, generally from about 1 µg to about 1000 mg per $cm^2$ skin per application, from about 2 µg to about 800 µg/$cm^2$ skin per application, from about 30 µg to about 700 µg/$cm^2$ skin, or from about 75 µg to about 250 µg/$cm^2$ skin. Application may from about four times a day to about twice a week, from about three times a day to about once every other day, from about once daily to about three times daily, once daily, twice daily or three times daily. Application for at least several days may be required to see a skin lightening effect (e.g., for at least 5 days, at least 6 days, at least 7 days, at least two weeks, at least three weeks or at least four weeks). After lightening is achieved, it may be possible to reduce the frequency and dosage frequency and dosage to a maintenance level, as desired. Such maintenance varies according to the individual, but may be from about 1/10 to about 1/2, or from about 1/5 to about 1/3 of the original dosage and/or frequency, as needed.

The following non-limiting examples serve to further illustrate the use of the agents of the present disclosure.

EXAMPLES

Example I

In a flask, 0.50 g of racemic deoxyArbutin was dissolved in 10 mL of 90:10 heptane/ethanol admixture. These compounds are then separated using an Agilent 1100 Prep HPLC system, with a elution solvent ratio of 94:6 heptane/ethanol and a 20×250 mm, 5u Chiralpak IA column, running 19 mL/min. The detection system is a UV lamp at 225 nm. 300 uL injections of the solution are sent through the column and the peaks separated either manually or by an automated fraction collector.

Example II

The chiral, non-racemic analog, (+) deoxyArbutin ((+)-dA), prepared as described in Example I is administered topically to a human in need of beautifying. After several weeks of twice daily treatments, the treated areas of the skin exhibit decreased pigmentation, and increased health and vitality.

Example III

In a flask, 0.50 g of racemic (+)-2-fluorodeoxyArbutin was dissolved in 10 mL of 90:10 heptane/ethanol admixture. These compounds are then separated using an Agilent 1100 Prep HPLC system, with an elution solvent ratio of 94:6 heptane/ethanol and a 20×250 mm, 5u Chiralpak IA column, running 19 mL/min. The detection system is a UV lamp at 225 nm. 300 uL injections of the solution are sent thru the column and the peaks separated either manually or by an automated fraction collector.

Example IV

A composition in liquid form is prepared by conventional methods, formulated as follows:

| Ingredient | Quantity |
|---|---|
| (+) thio-deoxyArbutin | 500 mg |
| (+) 2-chlorodeoxyArbutin | 500 mg |
| Propylene glycol | 5 ml |
| Ethyl alcohol | 5 ml |

1.0 mL of the above composition, when administered once a day, substantially increases the beauty and health of the mammalian skin onto which it is applied.

Example V

Figure 2:
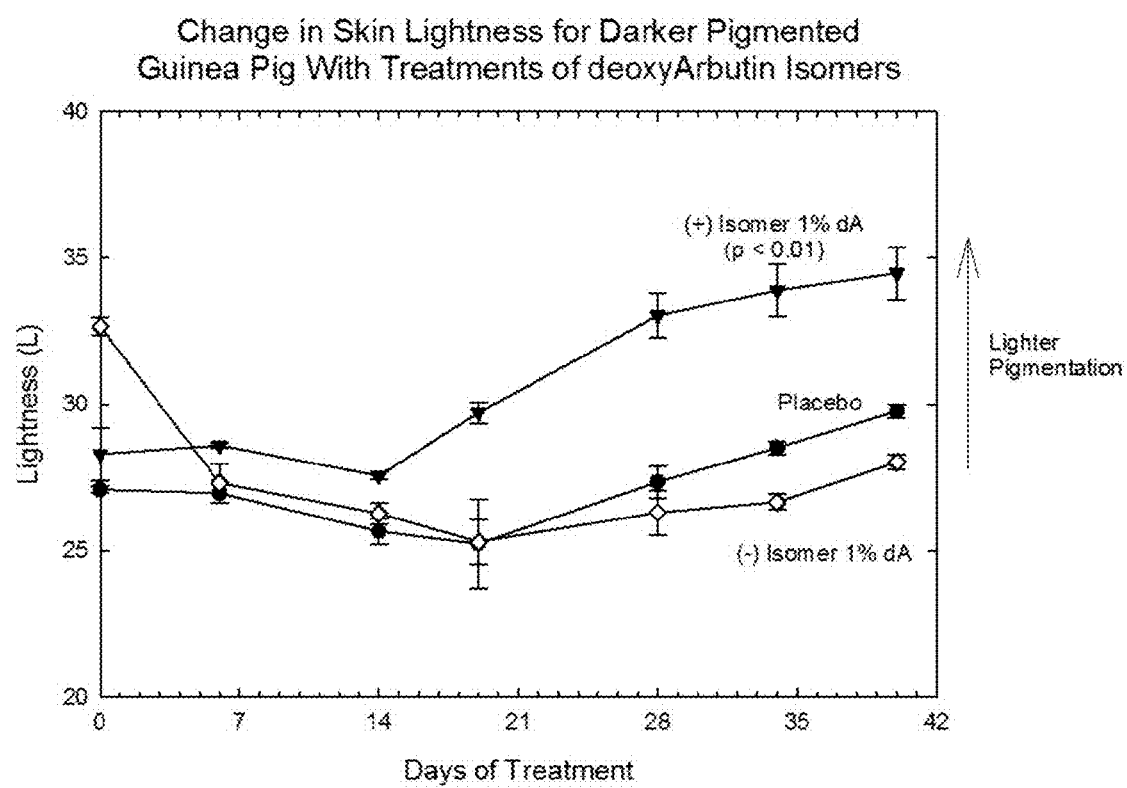
FIG. 2 is a graph illustrating the change in skin lightness of a darker pigmented guinea pig following treatment with (+) and (−) enantiomers of deoxyArbutin.
Figure 3:
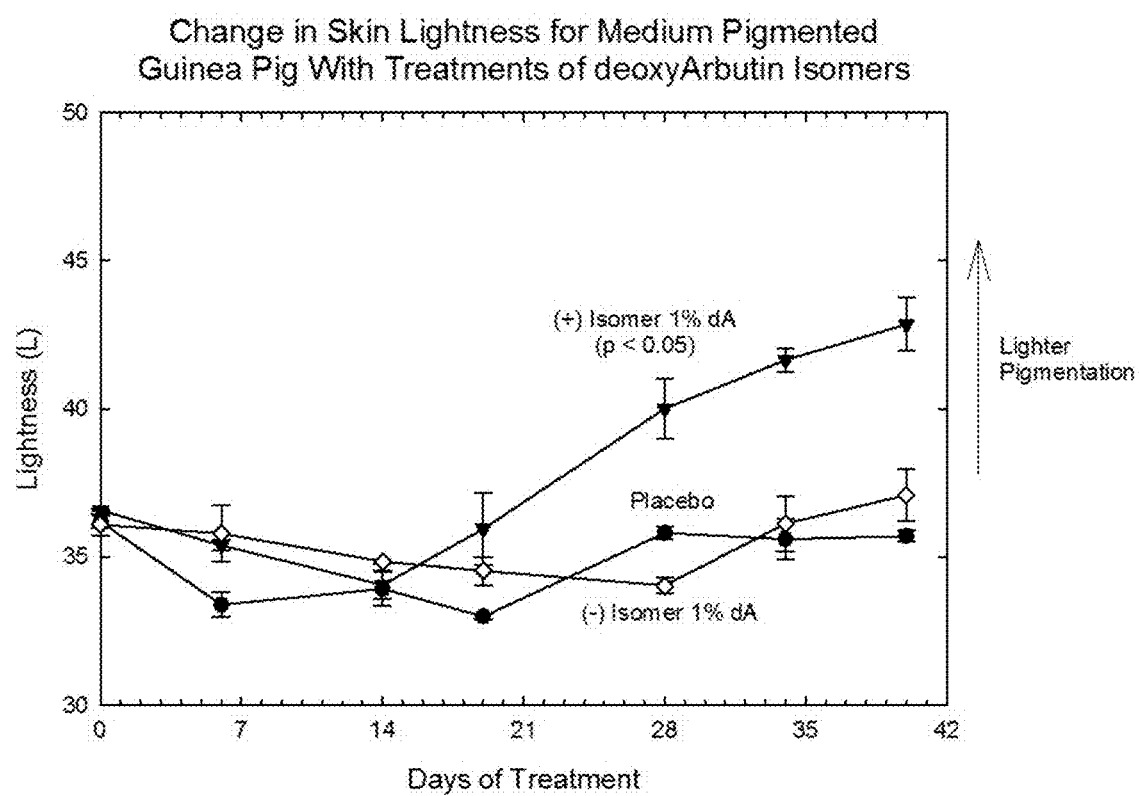
FIG. 3 is a graph illustrating the change in skin lightness of a medium pigmented guinea pig following treatment with (+) and (−) enantiomers of deoxyArbutin.
Figure 4:
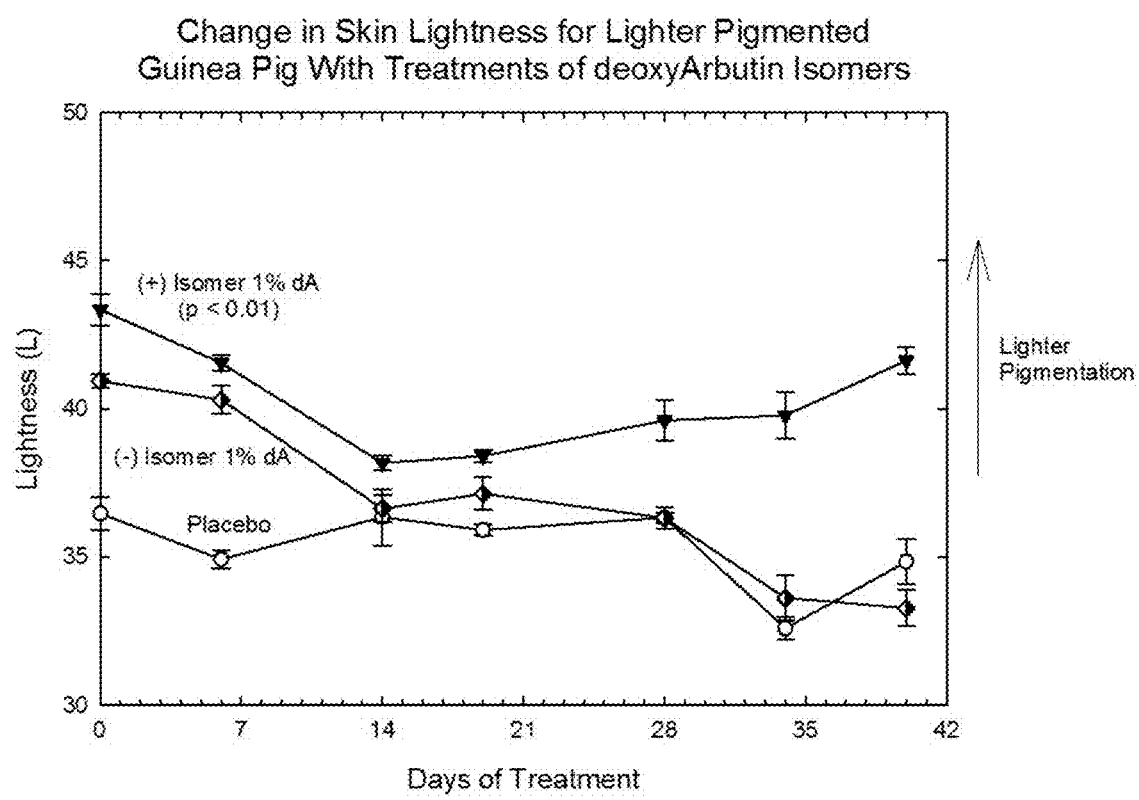
FIG. 4 is a graph illustrating the change in skin lightness of a lighter pigmented guinea pig following treatment with (+) and (−) enantiomers of deoxyArbutin.

Hairless pigmented guinea pigs were purchased, housed in cages, and treated according to GLP (good laboratory practices) under Veterinary care. Hairless guinea pigs with range of light/black skin pigmentation (e.g., lighter, medium, darker) were treated twice daily with 0.25 g of skin lotions (e.g., placebo, 1% deoxyArbutin (−) isomer, 1% deoxyArbutin (+) isomer) on 3.5 cm² treatment areas on the backs of the guinea pigs. All lotions were prepared under GMP (good manufacturing practice) conditions and passed all finished product specifications. At time zero and weekly for 6 weeks, the skin colors (Lab) were read by a Minolta Chromameter on three different areas within the treatment area. The laboratory area had low lightening so to minimize any impact of stray light on the L (Lightness) values. The Lab values were recorded into an Excel spreadsheet. Statistical analyses and graphs were created in Sigma Plot. Results are illustrated in FIGS. 2-4.

Example VI

Figure 5:
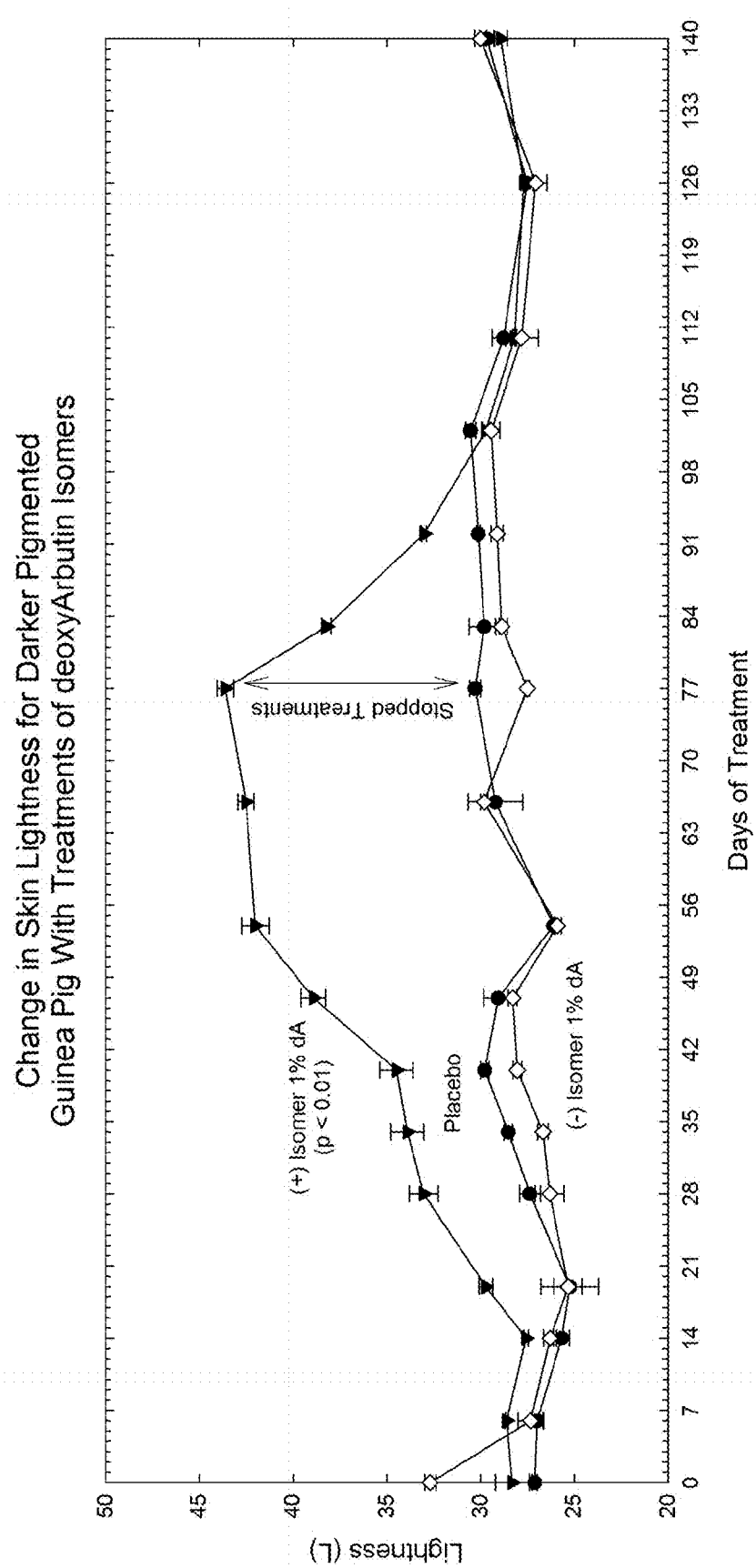
FIG. 5 is a graph illustrating the change in skin lightness of a darker pigmented guinea pig following treatment with (+) and (−) enantiomers of deoxyArbutin, both a period of twice-daily treatments, and after treatments were stopped.
Figure 6:
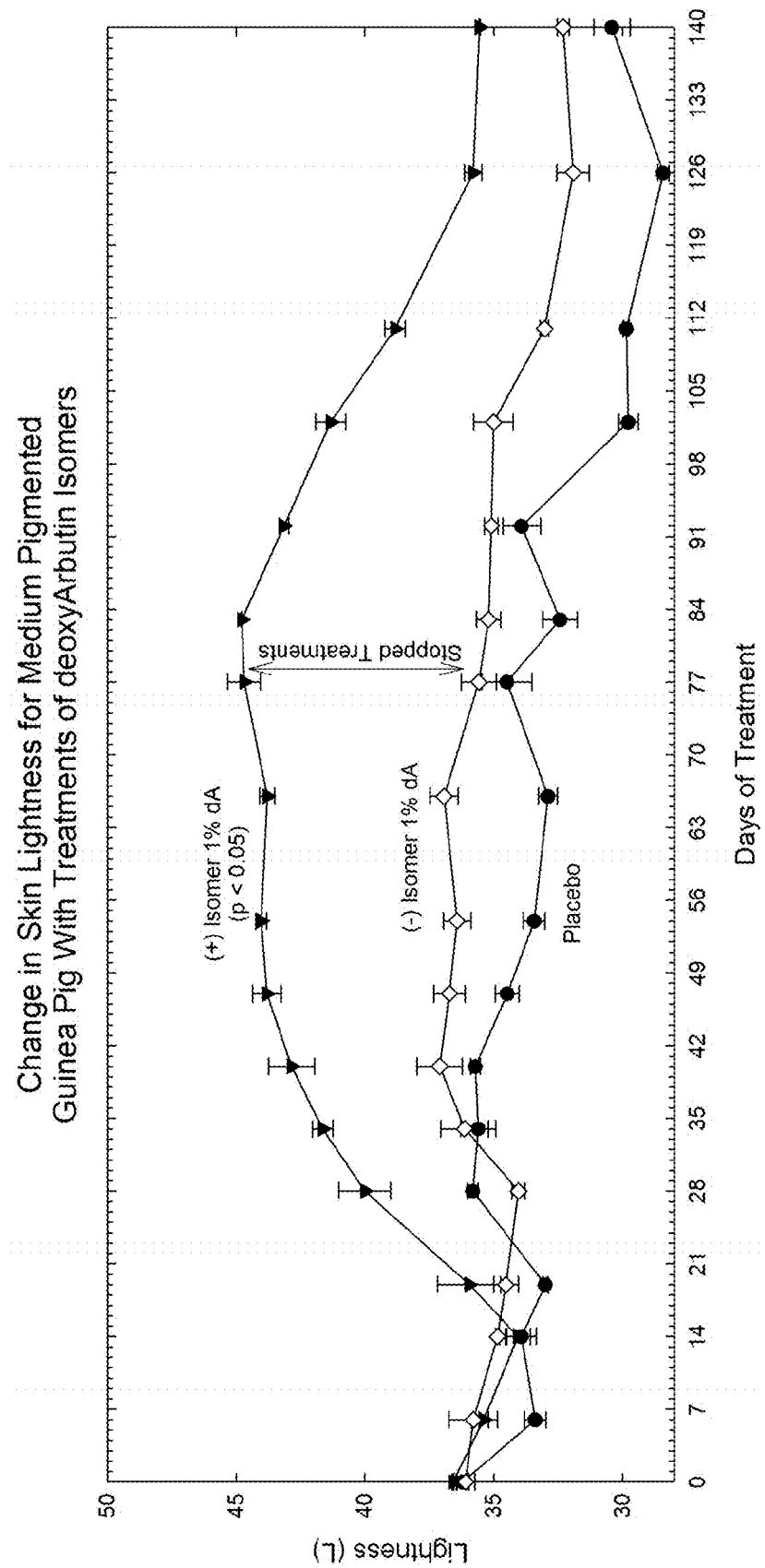
FIG. 6 is a graph illustrating the change in skin lightness of a medium pigmented guinea pig following treatment with (+) and (−) enantiomers of deoxyArbutin, both a period of twice-daily treatments, and after treatments were stopped.
Figure 7:
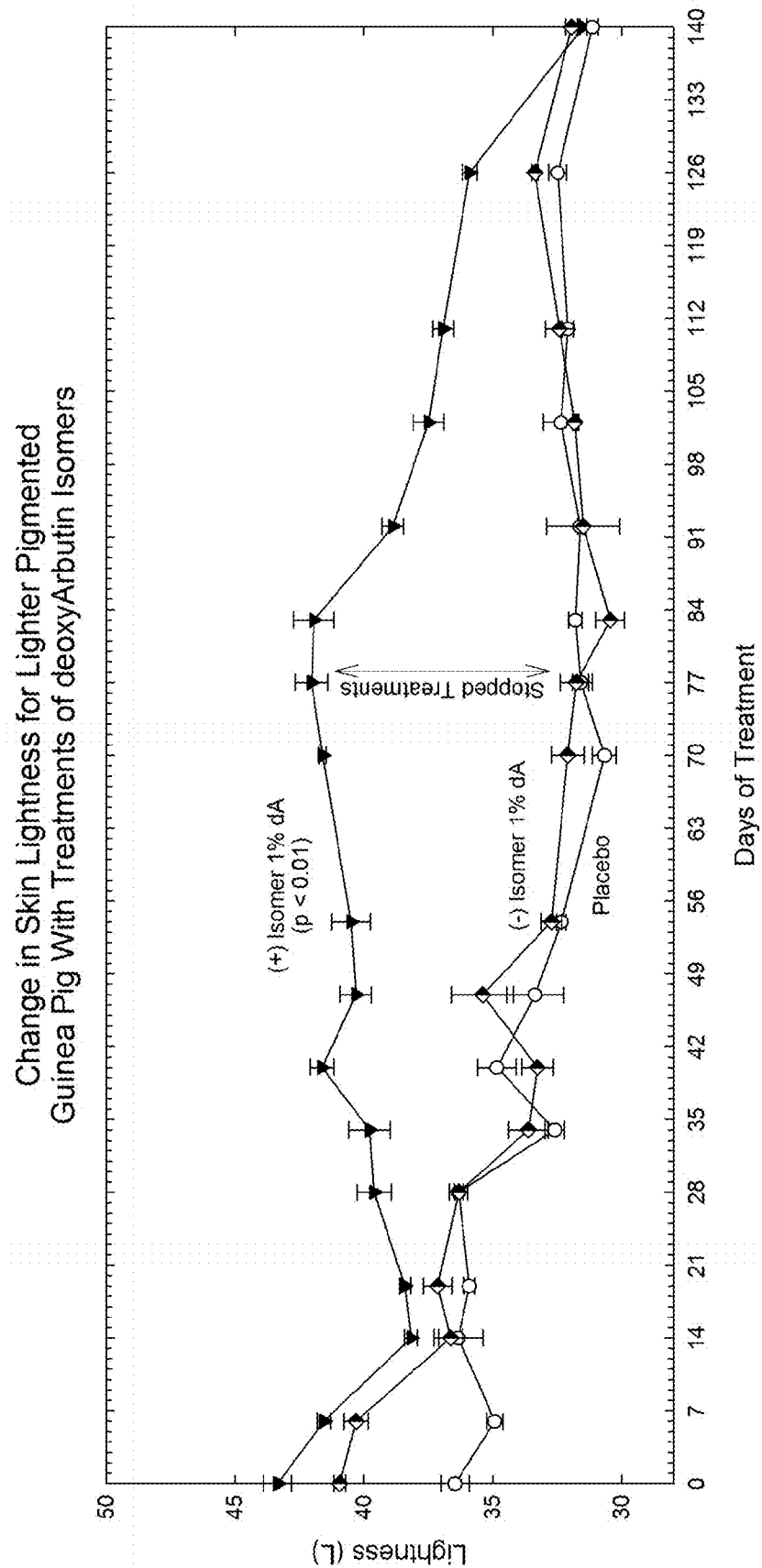
FIG. 7 is a graph illustrating the change in skin lightness of a lighter pigmented guinea pig following treatment with (+) and (−) enantiomers of deoxyArbutin, both a period of twice-daily treatments, and after treatments were stopped.

Hairless pigmented guinea pigs were purchased, housed in cages, and treated according to GLP (good laboratory practices) under Veterinary care. Hairless guinea pigs with range of light/black skin pigmentation (e.g., lighter, medium, darker) were treated twice daily with 0.25 g of skin lotions (e.g., placebo, 1% deoxyArbutin (−) isomer, 1% deoxyArbutin (+) isomer) on 3.5 cm² treatment areas on the backs of the guinea pigs. All lotions were prepared under GMP (good manufacturing practice) conditions and passed all finished product specifications. At time zero and weekly for 11 weeks, the skin colors (Lab) were read by a Minolta Chromameter on three different areas within the treatment area. The laboratory area had low lightening so to minimize any impact of stray light on the L (Lightness) values. Following the 11 weeks, the twice daily treatments were stopped, while the skin colors were recorded for another 9 weeks. The Lab values were recorded into an Excel spreadsheet. Statistical analyses and graphs were created in Sigma Plot. Results are illustrated in FIGS. 5-7.

What is claimed is:
1. A chiral, non-racemic compound of formula II-a:

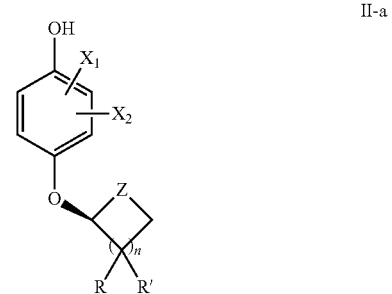

II-a or a pharmaceutically acceptable salt thereof;
wherein:
Z is selected from $NR_1$, S, O, SO and $SO_2$;
$R_1$ is selected from hydrogen and C1-6 aliphatic;
$X_1$ and $X_2$ are independently selected from hydrogen, halogen, cyano, nitro, optionally substituted C1-6 aliphatic, —$OR^2$, —$SR^2$, —$N(R^2)_2$, —$COOR^2$, and —$CON(R^2)_2$,
each $R^2$ is independently hydrogen or an optionally substituted C1-6 aliphatic;
n is 1, 2, 3, 4 or 5;
each R is independently selected from hydrogen and C1-6 aliphatic; and each R' is independently selected from hydrogen, C1-6 aliphatic and —OR$^a$, wherein each R$^a$ is independently selected from hydrogen and C1-6 aliphatic.

2. The compound of claim 1, wherein the compound has the formula II-b:

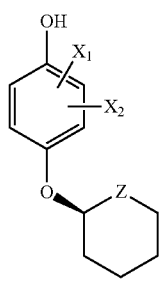

or a pharmaceutically acceptable salt thereof.

3. The compound of claim 1, wherein the compound has the formula II-c:

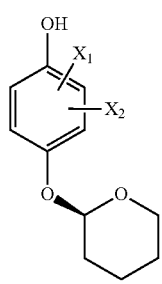

or a pharmaceutically acceptable salt thereof.

4. A chiral, non-racemic compound of formula II-d:

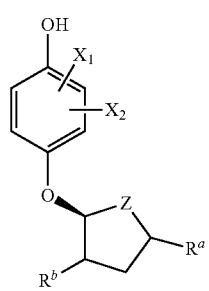

or a pharmaceutically acceptable salt thereof;
wherein:
Z is selected from NR$_1$, S, O, SO and SO$_2$;
R$_1$ is selected from hydrogen and C1-6 aliphatic;
X$_1$ and X$_2$ are independently selected from hydrogen, halogen, cyano, nitro, optionally substituted C1-6 aliphatic, —OR$^2$, —SR$^2$, —N(R$^2$)$_2$, —COOR$^2$, and —CON(R$^2$)$_2$;
each R$^2$ is independently hydrogen or an optionally substituted C1-6 aliphatic;
R$^a$ and R$^b$ are each independently selected from the group consisting of hydrogen, optionally substituted C1-6 aliphatic, and —OR$^2$, wherein R$^2$ is selected from the group consisting of hydrogen and optionally substituted C1-6 aliphatic.

5. The compound of claim 1, wherein the compound has the formula II-e:

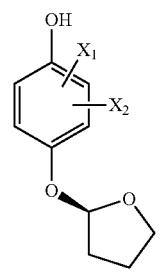

or a pharmaceutically acceptable salt thereof.

6. A chiral, non-racemic compound of formula II-f:

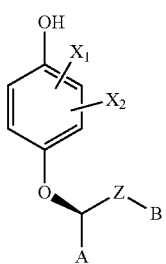

or a pharmaceutically acceptable salt thereof;
wherein:
Z is selected from NR$_1$, S, O, SO and SO$_2$;
R$_1$ is selected from hydrogen and C1-6 aliphatic;
X$_1$ and X$_2$ are independently selected from hydrogen, halogen, cyano, nitro, optionally substituted C1-6 aliphatic, —OR$^2$, —SR$^2$, —N(R$^2$)$_2$, —COOR$^2$, and —CON(R$^2$)$_2$;
each R$^2$ is independently hydrogen or an optionally substituted C1-6 aliphatic; and
A and B are independently an optionally substituted group selected from the group consisting of: C1-6 aliphatic; a 3-8 membered saturated carbocyclic ring; and phenyl.

7. A composition comprising a compound of claim 1 and a pharmaceutically acceptable carrier.

8. A product comprising a compound according to claim 1.

9. The product according to claim 8, wherein said product is a skin care composition.

10. The product according to claim 9, further comprising a dermatologically acceptable carrier.

11. The compound of claim 1, wherein the compound is (R)-4-((tetrahydro-2H-pyran-2-yl)oxy)phenol or a pharmaceutically acceptable salt thereof.

12. The compound of claim 11, wherein the compound has an enantiomeric excess of at least 50%.

13. The compound of claim 11, wherein the compound has an enantiomeric excess of at least 90%.

14. A composition comprising a compound of claim 11 and a pharmaceutically acceptable carrier.

15. A product comprising a compound according to claim 11.

16. The product according to claim 15, wherein said product is a skin care composition.

17. The product according to claim 16, further comprising a dermatologically acceptable carrier.

18. The compound of claim 1, wherein the compound has an enantiomeric excess of at least 50%.

19. The compound of claim 1, wherein the compound has an enantiomeric excess of at least 90%.

20. The compound of claim 1, wherein the compound has an enantiomeric excess of at least 50%.

21. The compound of claim 1, wherein the compound has an enantiomeric excess of at least 90%.

22. The compound of claim 3, wherein the compound has an enantiomeric excess of at least 50%.

23. The compound of claim 3, wherein the compound has an enantiomeric excess of at least 90%.

* * * * *